(12) United States Patent
Kim et al.

(10) Patent No.: US 9,045,744 B2
(45) Date of Patent: Jun. 2, 2015

(54) METHOD FOR USING AN ENZYME RESISTANT TO HIGH PRESSURES

(75) Inventors: Nam-Soo Kim, Seoul (KR); Chong-Tai Kim, Yongin-si (KR); Yong-Jin Cho, Seoul (KR); Chul-Jin Kim, Seongnam-si (KR); Jin-Soo Maeng, Changwon-si (KR); Soo-Jin Kwon, Seoul (KR)

(73) Assignee: Seiko Epson Corporation, Suwa-shi (JP)

( * ) Notice: Subject to any disclaimer, the term of this patent is extended or adjusted under 35 U.S.C. 154(b) by 0 days.

(21) Appl. No.: 14/000,497

(22) PCT Filed: Feb. 20, 2012

(86) PCT No.: PCT/KR2012/001256
§ 371 (c)(1),
(2), (4) Date: Aug. 20, 2013

(87) PCT Pub. No.: WO2012/115409
PCT Pub. Date: Aug. 30, 2012

(65) Prior Publication Data
US 2013/0330758 A1 Dec. 12, 2013

(30) Foreign Application Priority Data
Feb. 21, 2011 (KR) .................. 10-2011-0015253

(51) Int. Cl.
| | |
|---|---|
| *C12N 9/50* | (2006.01) |
| *C12Q 1/37* | (2006.01) |
| *C12N 9/64* | (2006.01) |
| *A61K 38/48* | (2006.01) |
| *A61K 38/51* | (2006.01) |
| *A23L 1/01* | (2006.01) |
| *A23L 1/03* | (2006.01) |
| *A23L 1/22* | (2006.01) |
| *A23L 1/227* | (2006.01) |
| *A23L 3/015* | (2006.01) |
| *C12N 9/48* | (2006.01) |
| *C12N 9/52* | (2006.01) |
| *C12N 9/76* | (2006.01) |

(52) U.S. Cl.
CPC ............. *C12N 9/6481* (2013.01); *C12Y 304/00* (2013.01); *A61K 38/48* (2013.01); *A61K 38/51* (2013.01); *A23L 1/0135* (2013.01); *A23L 1/034* (2013.01); *A23L 1/22* (2013.01); *A23L 1/227* (2013.01); *A23L 3/0155* (2013.01); *C12Q 1/37* (2013.01); *C12N 9/48* (2013.01); *C12N 9/485* (2013.01); *C12N 9/52* (2013.01); *C12N 9/6427* (2013.01)

(58) Field of Classification Search
USPC .................................... 435/183, 23; 530/350
See application file for complete search history.

(56) References Cited

PUBLICATIONS

Izquierdo et al., Food Chemistry, 92, 713-719, 2005.*
Athes et al., Biotechnology Letters, 19(3), 273-276, 1997.*
A. Laurence Curl et al., 'Effect of High Pressures on Trypsin and Chymotrypsin', Enzyme Research Division Contribution, 1949, No. 124. pp. 45-54.
Takashi Ohmori et al., 'Effect of High Pressure on the Protease Activities in Meat' Agricultural and Biological Chemistry, 1991, vol. '55, No. 2, pp. 357-361.

* cited by examiner

*Primary Examiner* — Maryam Monshipouri
(74) *Attorney, Agent, or Firm* — Nutter McClennen & Fish LLP; John J. Penny, Jr.; Taylor M. Coon

(57) ABSTRACT

At least at least one embodiment of the present invention relates to a method for using a high pressure-resistant enzyme in a high pressure condition; a method for promoting the activity of the high pressure-resistant enzyme by means of a high pressure treatment; a composition, which contains the high pressure-resistant enzyme, for decomposing proteins under a high pressure condition; a composition, which contains the composition for decomposing proteins, for preparing natural flavoring substances; a container for high pressure treatment, which contains the composition for decomposing proteins; and a method for measuring the activity of the high pressure-resistant enzyme, which comprises a step of decomposing an azocasein solution serving as a substrate by using the high pressure-resistant enzyme treated under a high pressure condition.

18 Claims, 31 Drawing Sheets

| Enzyme concentration (mg/mL) | Trypsin acetylated | α-Chymotrypsin | Ficin | Papain (papaya) | Papain (carica) | Thermolysin | Bromelain | Pepsin |
|---|---|---|---|---|---|---|---|---|
| 0.05 | 0.316±0.0107[a] | 0.143±0.0068 | - | - | - | 0.889±0.0318 | - | 0.037±0.0009 |
| 0.1 | 0.485±0.0136 | 0.205±0.0057 | - | - | - | 1.202±0.0054 | 0.007±0.0073 | 0.049±0.0030 |
| 0.5 | 0.891±0.0253 | 0.437±0.0165 | 0.253±0.0121 | 0.142±0.0081 | 0.058±0.0061 | 1.409±0.0081 | 0.066±0.0119 | 0.090±0.0027 |
| 1 | 1.058±0.0233 | 0.545±0.0099 | 0.745±0.0224 | 0.332±0.0143 | 0.184±0.0114 | 1.423±0.0064 | 0.153±0.0090 | 0.125±0.0028 |
| 5 | 1.332±0.0058 | 1.071±0.0041 | 1.434±0.0053 | 1.292±0.0067 | 1.162±0.0034 | 1.413±0.0037 | 0.687±0.0029 | 0.288±0.0080 |

[a] Mean±SD(n=3).

| Enzyme concentration (mg/mL) | Protamex | Protease E | Flavourzyme | Alcalase |
|---|---|---|---|---|
| 0.25 | 0.253±0.0030[a] | 0.095±0.0011 | 0.042±0.0019 | 0.460±0.0224 |
| 0.5 | 0.610±0.0092 | 0.231±0.0303 | 0.095±0.042 | 0.839±0.0059 |
| 2.5 | 1.370±0.0103 | 1.162±0.0112 | 0.676±0.0261 | 1.366±0.0124 |
| 5 | 1.414±0.0115 | 1.327±0.0072 | 1.113±0.0034 | 1.408±0.0051 |
| 25 | 1.437±0.0127 | 1.424±0.0009 | 1.444±0.0068 | 1.429±0.0011 |

[a] Mean±SD(n=3).

METHOD FOR USING AN ENZYME RESISTANT TO HIGH PRESSURES

CROSS-REFERENCE TO RELATED APPLICATIONS

The present application claims priority to Korean Patent Application No. 10-2011-0015253 filed in the Republic of Korea on Feb. 21, 2011, and PCT Application No. PCT/KR2012/001256 filed on Feb. 20, 2012, the disclosures of which are incorporated herein by reference.

TECHNICAL FIELD

The present invention relates to a method for using an enzyme under a high pressure condition, a method for promoting the activity of the enzyme; and a method for measuring the activity of the enzyme.

BACKGROUND

Enzymes do not have any kind of side reaction during physicochemical hydrolysis, have low energy consumption due to their high catalytic activity, and does not have to be removed after processing. Accordingly, they widely are used in various industries.

Enzymes in the past have been mainly used for food production using glycolysis saccharifying starch, but recently, their range of use has expanded to being used for producing medicine, fine chemical products, and food, drugs and chemicals for special use. Specifically, food enzymes are being used in a variety of fields such as syrup production, alcohol fermentation such as beer, dairy, bread, fruit and vegetable juice production, crop-processing, food preservation, egg-processing, food lipid-processing, fish-processing, flavor production, animal feed production. Further, they are also being used as a detergent, with the trend increasing towards the use of enzyme as a dishwashing detergent, which has largely contributed to the growing market for using enzymes as a detergent. Recently, the use of the enzymes in the textile industry has also gradually increased. Accordingly, in the case of wool, a biocarbonsation process, which removes impurities existing in the fibers by using enzymes, is being developed, and the enzymes are also used in a polishing process, which removes naps on the textile, for improving clearness of dyeing, visibility of colors, feel of the surface, wrinkle resistance and softness. In the case of pulp, the enzymes are also used for removing impurities, and the enzymes also may be used in a deinking process, which removes ink when recycling printed papers. In the case of the leather industry, which is a representative industry for causing environmental pollution, a process for using the enzymes instead of strong acid during soaking, unhairing or defatting process, are being developed in order to solve the said problem. In addition, the enzymes are also used in various chemical industries such as amino acid industry, steroid conversion, antibiotic material production, peptide synthesis, ester conversion and synthesis, and organic chemistry. Furthermore, as therapeutic enzymes, digestive enzymes, anti-inflammatory enzymes, thrombolytic enzymes, anti-tumor enzymes, enzymes for the circulating system and the like are being developed, and clinical diagnosis field using enzymes are also being developed step by step. Particularly, in Korea, enzymes are often used because an enzyme hydrolysis method, which produces animal and vegetable protein hydrolysates through protein hydrolysis by directly adding enzymes to raw materials is used in order to prepare traditional natural flavoring substances.

On the other hand, under high pressure, a chemical reaction is stimulated toward the direction where volume is decreased, according to the LE Chartelier's principle. Thus, the reaction may be accelerated when the volume is decreased according to the increased pressure. Accordingly, for the purpose of accelerating the reaction using various enzymes described above, a high pressure process is used. Particularly, when conducting reactions for producing foods under the high pressure condition, it may affect the hydrogen bonds, thereby changing three dimensional structures of macro molecules, which will maintain the natural flavor, taste, color and nutritional ingredients, increase solubility and extraction rate, and also improve preservation. In addition, when using the high pressure process, high-quality foods may be produced so that functional characteristics are excellent and nutritional ingredients are preserved. Such a high pressure process is an eco-friendly economic process with low energy consumption. When using the high pressure process, there are advantages in that growth of microorganisms may be inhibited, the enzyme function is stimulated, the treatment process is simple, and addition of additive salt and alcohol may be excluded. For example, when producing extracts such as red ginseng extract, green tea extract, bamboo extract and adlay extract, if the high pressure enzyme reaction is used, the effect and physical properties of the extract may be changed.

However, generally under the high pressure condition, water penetrated into the tertiary structure of the enzyme may destruct the bonding force of the tertiary structure (e.g., hydrophobic bond), which will make it lose its enzyme activity making it difficult to use the enzymes under high pressure condition.

SUMMARY

The present invention is designed to solve the problems of the prior art, and therefore it is an object of at least at least one embodiment of the present invention to provide a method for using a high pressure-resistant enzyme in a high pressure condition; a method for promoting the activity of the high pressure-resistant enzyme by improving the thermal stability of the enzyme by means of a high pressure treatment; a composition, which contains the high pressure-resistant enzyme, for decomposing proteins under a high pressure condition; a composition, which contains the composition for decomposing proteins, for preparing natural flavoring substances; a container for high pressure treatment, which contains the composition for decomposing proteins; and a method for measuring the activity of the high pressure-resistant enzyme, which comprises a step of decomposing an azocasein solution serving as a substrate by using the high pressure-resistant enzyme treated under a high pressure condition.

In order to solve the above problems, as one embodiment, the present invention relates to a method for using an enzyme under a high pressure condition, wherein the enzyme is at least one selected from the group consisting of α-chymotrypsin, pepsin, trypsin, trypsin acetylated, flavourzyme, protease E (preferably, Marugoto E™) and alcalase.

More preferably, the high pressure condition may be 100 to 400 MPa.

The present inventors confirmed that α-chymotrypsin, pepsin, trypsin and trypsin acetylated are excellent in pressure resistance, with the trypsin being the most excellent in that when treated at high pressure of 300 MPa for 300 min, the enzyme activity increased 40% compared with the trypsin treated at ambient pressure, as well as enzyme activity increasing at 300 MPa as time passed. Further, the α-chymotrypsin showed a tendency to increase the enzyme activity at 300 MPa as time passed, and when it was treated at high pressure for 300 min, its relative activity was over 100%. Further, the trypsin acetylated also showed a tendency to increase the enzyme activity at 300 MPa as time passed, and when treated at high pressure for 300 min, its relative activity was also 100%, which was almost similar to the case in which it was treated at ambient pressure for 300 min. Further, the pepsin treated at high pressure also showed the same enzyme activity with the case when treated at ambient pressure.

In addition, it was confirmed that flavourzyme, protease E and alcalase were also excellent in pressure resistant characteristic. When the flavourzyme and the protease E were treated at high pressure for 300 min, its enzyme activity was almost similar with when treated at ambient pressure, and its relative activity was about 100%. Further, the alcalase was also excellent in pressure resistance. Accordingly, when it was treated at high pressure of 300 MPa for 300 min, it showed almost similar enzyme activity with the alcalase treated at ambient pressure for the same duration, and also showed a tendency to increase the relative activity at 300 MPa as time passed.

Therefore, the present invention was completed by finding that the α-chymotrypsin, pepsin, trypsin, trypsin acetylated, flavourzyme, protease E and alcalase have high pressure resistance (see FIGS. 7 to 10).

According to at least at least one embodiment of the present invention, by means of using the high pressure-resistant enzymes, a method for using the enzymes under a high pressure condition while keeping the enzyme activities, preferably reactions, such as protein decomposition, carbohydrate decomposition, lipid decomposition, bioactive compound extractions, protein enzyme modification, enzyme synthesis for functional ingredients and the like, under a high pressure condition may be conducted. More preferably, the bioactive compound extraction may be extracting the bioactive compounds from plants having thick cell walls, the protein enzyme modification may be objected to improve digestibility and the like, and in the enzyme synthesis for functional ingredients, the functional ingredients may include sweeteners, peptides, enantio selective esters and the like.

In addition, the method for using the enzymes may be more favorable for accomplishing the object of using the enzymes when the activities of the enzymes are promoted. Accordingly, the method for using enzymes, preferably reactions, such as protein decomposition, carbohydrate decomposition, lipid decomposition, bioactive compound extractions, protein enzyme modification, enzyme synthesis for functional ingredients and the like, under a high pressure condition may be applied to a method for promoting the activities of the enzymes.

Therefore, as another embodiment, the present invention provides a composition for decomposing proteins, a composition for decomposing carbohydrates, a composition for decomposing lipids, a composition for extracting bioactive compounds, a composition for modifying protein enzymes or a composition for synthesizing functional ingredients with enzymes, which contains at least one enzyme selected from the group consisting of α-chymotrypsin, pepsin, trypsin, trypsin acetylated, flavourzyme, protease E and alcalase, under a high pressure condition. Preferably, the high pressure condition may be 100 to 400 MPa.

The term "protein decomposition", used herein refers to a chemical reaction making amino acids or peptide mixtures by hydrolyzing peptide bonds of proteins and peptides.

The term "high pressure resistance", used herein refers to a characteristic in which the activity is maintained or increased under a high pressure condition, and the high pressure may be 100 MPa or more, preferably 100 to 400 MPa, more preferably 100 to 300 MPa.

The α-chymotrypsin, pepsin, trypsin, trypsin acetylated, flavourzyme, protease E and alcalase are known as an enzyme, and can be easily obtained in the art through commercial routes. The α-chymotrypsin may be one derived from bovine pancreas, the pepsin may be one derived from pig gastric mucous membrane, the trypsin may be one derived from bovine pancreas, the trypsin acetylated may be one derived from bovine pancreas, the flavourzyme may be one derived from Aspergillusoryzae, the protease E may be one derived from microorganisms, or the alcalase may be one derived from *Bacillus licheniformis*, preferably, but is not limited thereto. Preferably, the protease E may be Marugoto E™, but is not limited thereto.

It was estimated that among the said enzymes, serine-based enzymes, alcalase, α-chymotrypsin, trypsin and trypsin acetylated, have a common acyl-enzyme intermediate as a covalent intermediate, and since covalent bondings at their active site are not destructed even when treated at high pressure, the bondings are estimated to contribute to maintaining the enzyme activity (see FIG. 11). On the contrary, in the case of thermolysin, which is a metalloprotease, a zinc ion is essential for expressing the activity of the enzyme. It is estimated that the zinc ion is coordinately bonded to amino acids on an active site, and the coordinate bondings are destructed when treated at high pressure, which will make it lose its enzyme activity (see FIG. 12). But, for this reason, it is not limited to only covalent bonds existing at the active site of all of the α-chymotrypsin, pepsin, trypsin, trypsin acetylated, flavourzyme, protease E and the alcalase, and the present invention is not construed to be limited by these assumptions or guesses.

Proper enzyme may be selected depending on the type of the substrate, and at least one selected from the group consisting of α-chymotrypsin, pepsin, trypsin, trypsin acetylated, flavourzyme, protease E and alcalase may be used alone or in a mixture thereof. If used in a mixture, the enzymes may be used simultaneously or sequentially. The present inventors confirmed that when the mixture of the high pressure-resistant enzymes was used, the enzyme hydrolysis improved, and particularly, the enzyme hydrolysis improved in proportion to the number of the enzyme to be mixed (see Tables 8 to 10). Accordingly, preferably, a mixture of two or more selected from the group consisting of α-chymotrypsin, pepsin, trypsin, trypsin acetylated, flavourzyme, protease E and alcalase may be used. More preferably, a mixture of three or more, four or more, five or more, or six or more, and most preferably, a mixture of seven or more may be used.

Further, if the activity of the enzyme used in the present invention is maintained, it may also include being chemically or physically treated before use, as well as being treated at high pressure treatment before use.

In at least at least one embodiment of the present invention, the pressurizing time (PT, time to maintain a certain pressure after reaching the pressure) of the high pressure condition may be properly selected by a person skilled in the art depending on the type of the substrate to be hydrolyzed, a method for using the enzyme, the type of the enzyme, the type of the solvent and the like, and the enzyme may maintain its high pressure resistance for 60 min or more at 100 to 400 MPa, preferably 60 to 300 min, and therefore, the PT may be 60 min or more, for example, 60 to 300 min.

In at least at least one embodiment of the present invention, although the high pressure may be formed by various methods known in the art such as gas, heat and liquid, it may more preferably be hydraulic pressure formed by water.

The present invention may be conducted in both an open-type reaction system and a closed-type reaction system, but more preferably the closed-type reaction system may be used to prepare natural flavoring substances in order to improve flavor. For example, the reaction may be conducted in the high pressure enzyme hydrolysis system illustrated in FIG. 1, but is not limited thereto.

Further, in at least at least one embodiment of the present invention, the reaction temperature may be properly selected by a person skilled in the art depending on the type of the substrate to be hydrolyzed, a method for using the enzyme, the type of the enzyme, the type of the solvent and the like, but the reaction rate and/or the reaction yield may be increased by heating in the temperature range where the enzyme and the substrate are not denatured.

Particularly, the present inventors confirmed that the thermal stability of the enzyme largely increased after the high pressure treatment, and therefore, the enzyme activity improved when heated under high pressure condition, compared with the ambient pressure condition (Tables 3 to 6, FIGS. 13 to 16). Accordingly, when using the high pressure-resistant enzyme, the yield of the heat-treated reaction under the high pressure condition, for example, the yield of protein hydrolysate may be improved.

The heat treatment may include heating at 40° C. or higher for 2 min or longer, preferably at 40 to 85° C. or higher for 2 min or longer, more preferably at 40 to 85° C. or higher for 2 to 120 min.

Therefore, as another embodiment, the present invention provides a method for improving the activity of at least one enzyme selected from the group consisting of α-chymotrypsin, pepsin, trypsin, trypsin acetylated, flavourzyme, protease E and alcalase, wherein the enzyme is treated at high pressure when heating. Preferably, the high pressure condition may be 100 to 400 MPa, and more preferably 100 to 300 MPa.

The high pressure treatment and the heat treatment may be conducted simultaneously or independently. When conducted independently, they may be conducted sequentially, and the high pressure treatment may precede the heat treatment. But it is preferred that they be conducted simultaneously.

Natural flavoring substances may be prepared by using the method and the composition according to the present invention. Accordingly, as another embodiment, the present invention relates to a method for preparing natural flavoring substances, which comprises a step of hydrolyzing proteins under the high pressure condition by using the high pressure-resistant protein hydrolysis enzyme, and a composition for preparing natural flavoring substances, which comprises the composition for hydrolyzing proteins under the high pressure condition. Namely, at least at least one embodiment of the present invention provides the method for preparing natural flavoring substances, which comprises a step of reacting at high pressure by using at least one enzyme selected from the group consisting of α-chymotrypsin, pepsin, trypsin, trypsin acetylated, flavourzyme, protease E and alcalase, and the natural flavoring substances prepared by the said method. Preferably, in this method, the said heat treatment (for example, heating at 40° C. or higher for 2 min or longer) may be conducted at the same time. Preferably, the high pressure condition may be 100 to 400 MPa.

During the preparing process, any natural flavoring substance, which may include a step of hydrolyzing proteins by a protein hydrolysis enzyme, may be included in the said natural flavoring substances.

Other processes other than the step of hydrolyzing proteins may be properly selected by a person skilled in the art depending on the type of the natural flavoring substances to be prepared.

The method for preparing natural flavoring substances and the composition for preparing natural flavoring substances are exemplified as the method for hydrolyzing proteins and the composition for hydrolyzing proteins according to the present invention. It should be appreciated by those skilled in the art that the present invention is not limited to the exemplary uses and may be applied to other various uses and such equivalent uses do not depart from the spirit and scope of the invention.

As further another embodiment, the present invention relates to a container for high pressure treatment, which comprises the composition according to the present invention. Preferably, the high pressure condition may be 100 to 400 MPa.

The container may be any container, if it is durable to the high pressure treatment, and high pressure can be transferred into the container, regardless of shapes, structures and materials.

The container for high pressure treatment containing the high pressure-resistant enzymes may be applied to various uses because it can conduct treatments using the high pressure-resistant enzymes even under the high pressure treatment condition.

As further another embodiment of the present invention, the present invention related to a method for measuring the activity of the enzyme, which comprises a step of hydrolyzing an azocasein solution serving as a substrate by using the enzyme, which is at least one selected from the group consisting of α-chymotrypsin, pepsin, trypsin, trypsin acetylated, flavourzyme, protease E and alcalase, and treated under a high pressure condition. Preferably, the high pressure condition may be 100 to 400 MPa.

The present inventors confirmed that the activities of the enzymes treated at high pressure may be easily and accurately measured by using the azocasein solution as a substrate (FIG. 4). The said enzymes have the substrate specificity to various substrates including azocasein.

The concentration of the azocasein may be 2 to 5%, preferably 3%.

As seen from the above, according to at least at least one embodiment of the present invention, the reaction rate and/or reaction yield of a method for using an enzyme may be improved. Therefore, the present invention is expected to be used in various industry fields, and particularly, if it is used for producing food favoring substances, it is expected to bring significant changes in the entire food material industries using enzymes.

BRIEF DESCRIPTION OF THE DRAWINGS

Other objects and aspects of the present invention will become apparent from the following descriptions of the embodiments with reference to the accompanying drawings in which.

DETAILED DESCRIPTION

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Example 1

Constructing and Using High Pressure Enzymatic Hydrolysis System (High Pressure Bio-Hydrolysis Enzyme Reactor)

Figure 1:
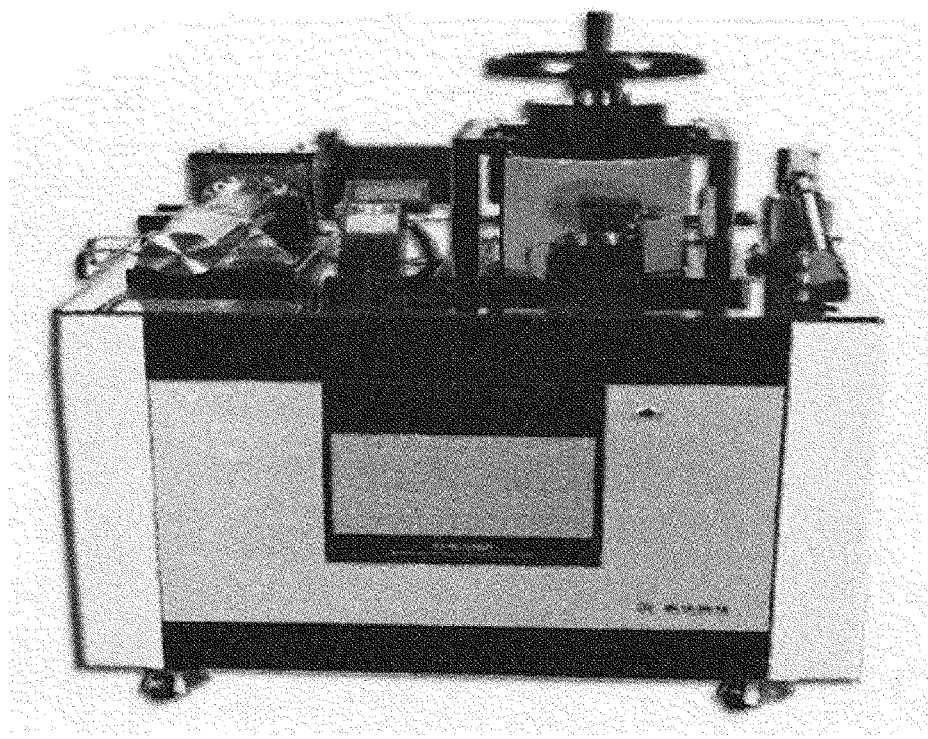
FIG. 1 shows a high pressure enzyme hydrolysis system (high pressure bio-hydrolysis enzyme reactor)

A high pressure enzymatic hydrolysis system was constructed in order to conduct a high pressure bio-hydrolysis reaction by an enzyme by means of hydraulic pressure, which was generated from water used as a pressure medium (see FIG. 1). This system, whose workable maximum reaction temperature and pressure were 70° C. and 4000 bar (400 MPa), respectively, was able to conduct various high pressure hydrolysis reaction by food enzymes, objected by the present study, and was able to increase in enzymatic hydrolysis and in production yield of the hydrolyzed products in a short time, by promoting enzyme activities and changing structures of hydrolysis substrates under a high pressure condition. By using a closed-type reaction system, flavors of reaction products such as salt-free natural flavoring substances were able to be enhanced.

Example 2

Securing Various Enzyme Groups

Enzymes, which will be used for producing natural flavoring substances by using the high pressure bio-hydrolysis technology were secured as follows, based on industrial enzymes and catalog enzymes.

A. Catalog Enzymes

Pepsin (from porcine gastric mucosa), trypsin (from bovine pancreas), α-chymotrypsin (from bovine pancreas), thermolysin (from *Bacillus thermoproteolyticus* rokko), papain (from papaya latex), papain (from *Carica papaya*), bromelain (from pineapple), trypsin (acetylated), ficin (from fig tree).

B. Industrial Enzymes

Alcalase 2.4 L (subtilisin, from *Bacillus licheniformis*, Novozyme), flavourzyme (aminopeptidase, from *Aspergillus oryzae*, Novozyme), Protamex (from *Bacillus licheniformis* and *B. amyloliquefaciens*, Novozyme), protease E (from microorganisms, Supercritical technology research corporation, Toyo Koatsu Co. Ltd.)

Example 3

Constructing Enzyme Activity Evaluation System

Figure 2:
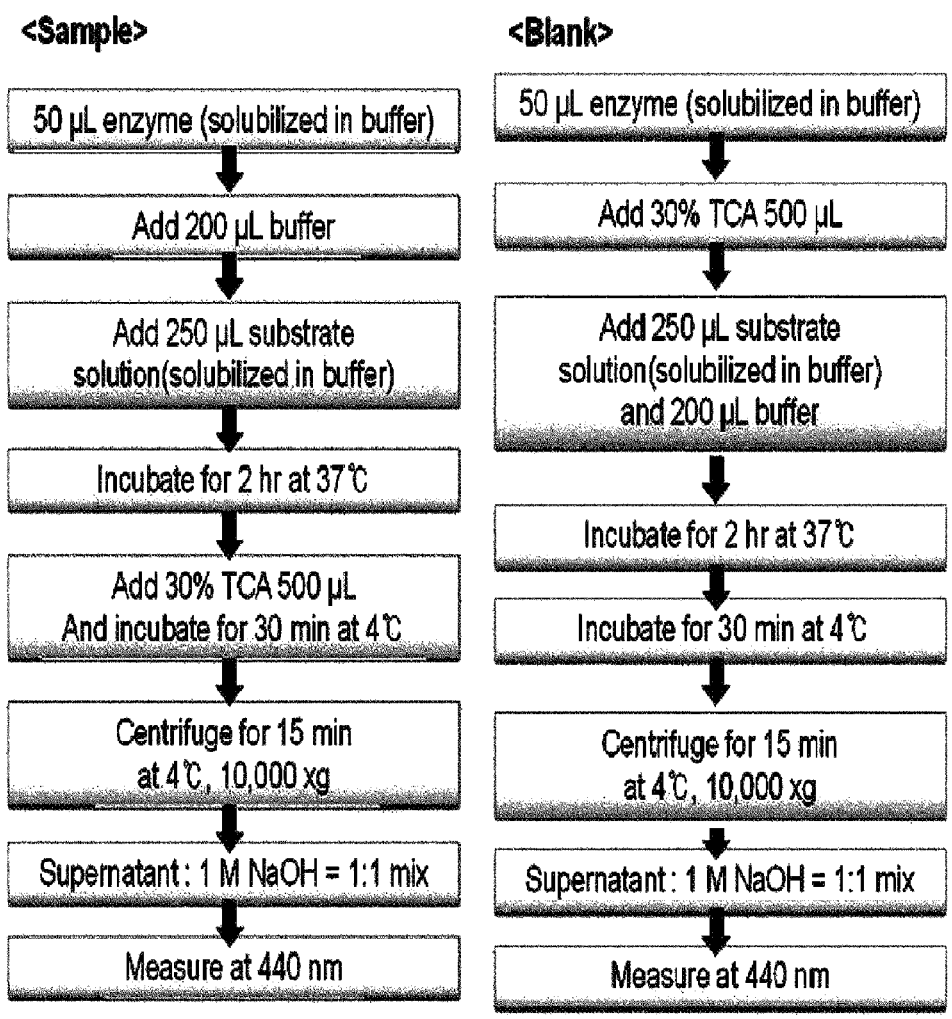
FIG. 2 shows a method for evaluating the enzyme activity. The sample is the case of activating an enzyme, and the blank is the case of inactivating an enzyme.
Figure 3:
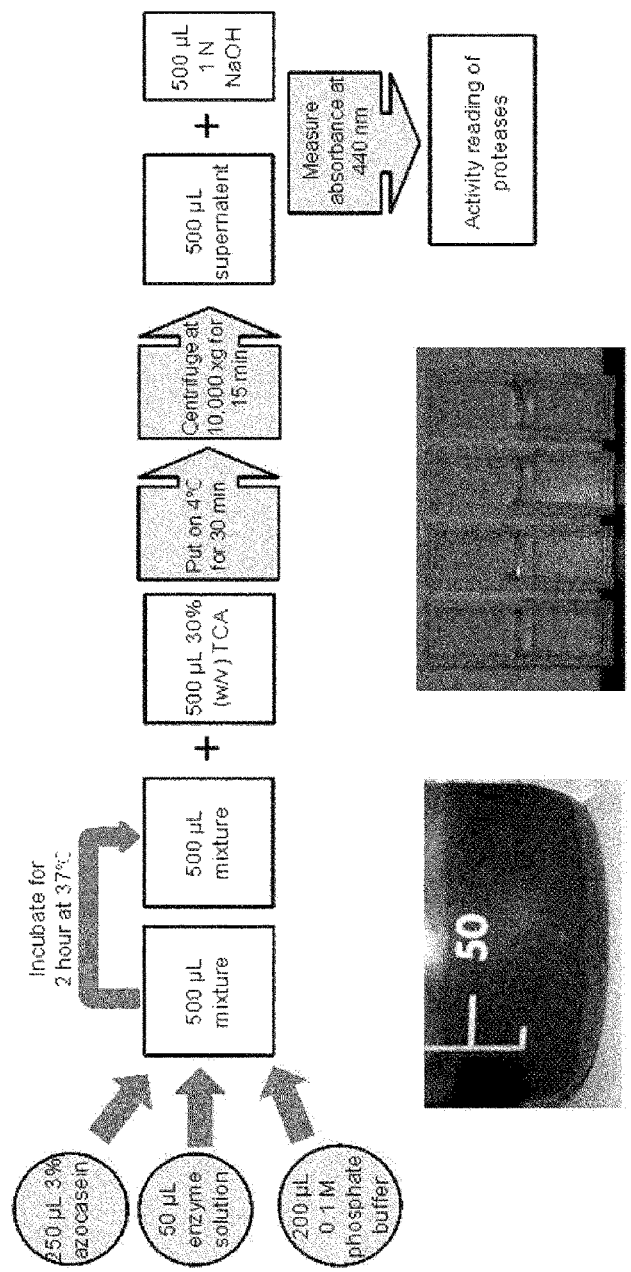
FIG. 3 shows a method for measuring the enzyme activity by using azocasein as a substrate.

Enzyme activities were searched over azoalbumin and azocasein combined with an azo dye as a chromogen. An advantage of this method is that the enzyme activity evaluation can be easily and accurately conducted. At this time, blank was an enzyme solution inactivated with 30% TCA solution in advance, and then treated in the same manner as the samples (see FIG. 2). Entire experiment processes were illustrated as shown in FIG. 3.

Example 4

Measuring Enzyme Activity Change Depending on Reaction Variables and High Pressure Condition A. Optimizing Substrate Concentration for Enzyme Reaction The substrate concentration for measuring the enzyme activity was optimized in order to test the change on the enzyme activity depending on the high pressure condition against the hydrolysis enzyme group secured above. Trypsin was dissolved in 0.1 M phosphate buffer solution (pH 7.5) at concentrations of 0.5 and 5 mg/mL, and then the enzyme activity was measured via the process illustrated in FIG. 3 while changing the substrate concentration from 0.2 to 9.5% (w/v).

Figure 4:
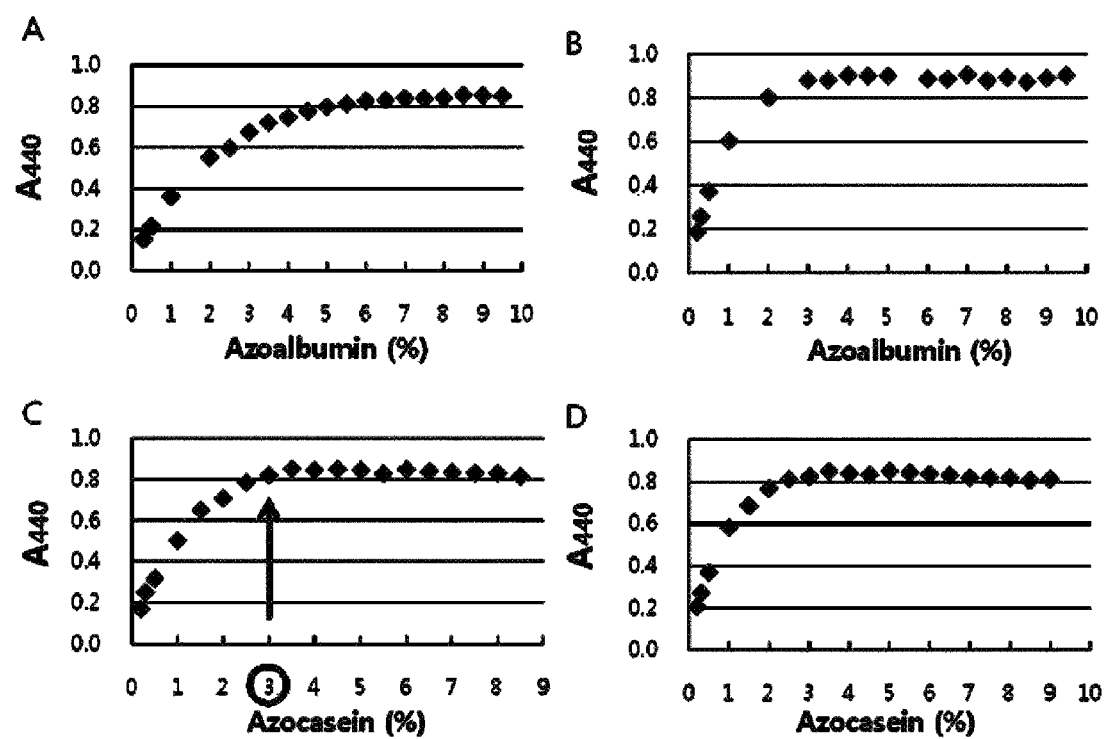
FIG. 4 shows the optimized substrate concentration for enzyme analysis (Trypsin concentrations (mg/mL): A, 0.5; B, 5; C, 0.5; D, 5)

While changing the substrate concentration, the enzyme activity was measured, and the result obtained there from showed a typical saturation curve (FIG. 4). The lowest concentration in the substrate concentration region where the saturation curve began to appear was selected as the optimum substrate concentration to avoid the $K_M$ region which has a big activity dynamic range according to the increase of the substrate concentration. The enzyme activity of trypsin was saturated at the azoalbumin concentration of 3% when trypsin concentration was 5 mg/mL, but in the case of azocasein, the enzyme activity of trypsin was saturated at the trypsin concentration of 0.5 mg/mL. Thus, it was observed that the reactivity of azocasein was better than that of azoalbumin. Accordingly, the 3% azocasein solution was used as a substrate solution in the later experiments.

B. Optimizing Enzyme Concentration for High Pressure Reaction

Then, in order to determine the enzyme concentration for high pressure treatment, the enzyme activity according to the concentration change was measured with the 3% azocasein as a substrate solution under the conditions of Table 1.

TABLE 1

Design for Test for Selecting Enzyme Concentration of High Pressure Treatment

| Enzyme | Temperature (° C.) | pH | Enzyme concentration (mg/mL) |
|---|---|---|---|
| Pepsin[a] | 37 | 0.01N HCl | 0.05, 0.1, 0.5, 1, 5 |
| α-Chymotrypsin[a] | 37 | 7.5 | 0.05, 0.1, 0.5, 1, 5 |
| Papain (from *papaya* latex)[a] | 37 | 6.5 | 0.05, 0.1, 0.5, 1, 5 |
| Papain (from *Carica papaya*)[b] | 37 | 6.5 | 0.05, 0.1, 0.5, 1, 5 |
| Bromelain[a] | 37 | 5 | 0.05, 0.1, 0.5, 1, 5 |
| Trypsin acetylated[c] | 37 | 7.5 | 0.05, 0.1, 0.5, 1, 5 |
| Thermolysin[a] | 37 | 7.5 | 0.05, 0.1, 0.5, 1, 5 |
| Trypsin[a] | 37 | 7.5 | 0.5 |
| Ficin[a] | 37 | 6.5 | 0.05, 0.1, 0.5, 1, 5 |
| Flavourzyme 500 MG[d] | 37 | 6.5 | 0.25, 0.5, 2.5, 5, 25 |
| Protamex[d] | 37 | 7 | 0.25, 0.5, 2.5, 5, 25 |
| Alcalase 2.4L[e] | 37 | 7.5 | 0.25, 0.5, 25, 5, 25 |
| Protease E[d] | 37 | 7 | 0.25, 0.5, 2.5, 5, 25 |

[a]Lyophilized powder,
[b]powder,
[c]synthetic,
[d]crude powder,
[e]liquid

Figure 5:
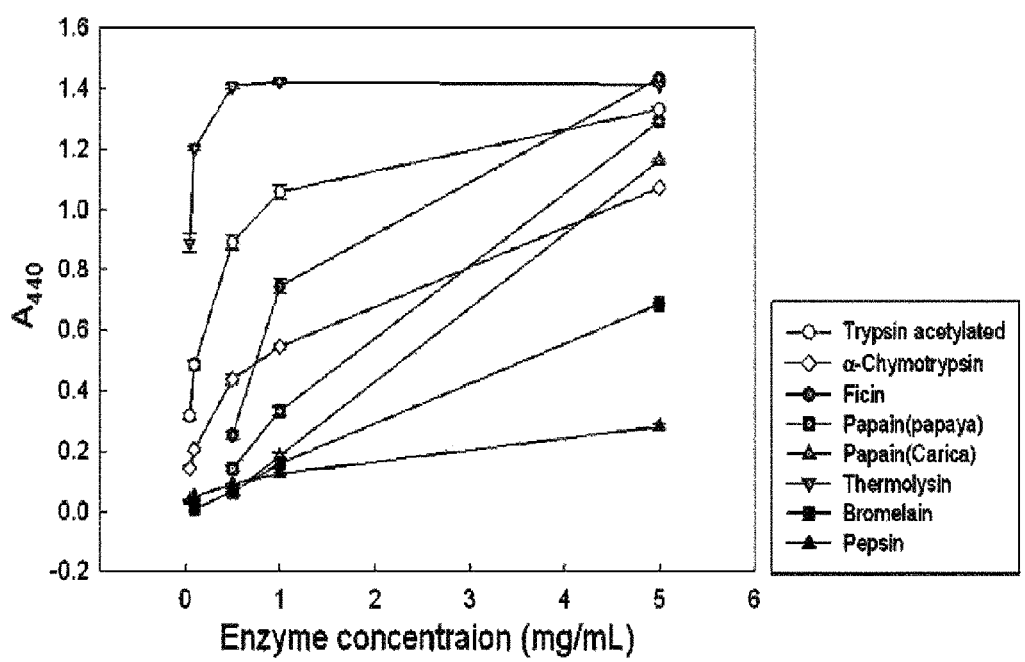
FIG. 5 shows the effects of the concentrations of catalog hydrolysis enzymes on the activity, measured by the azocasein analysis.
Figure 6:
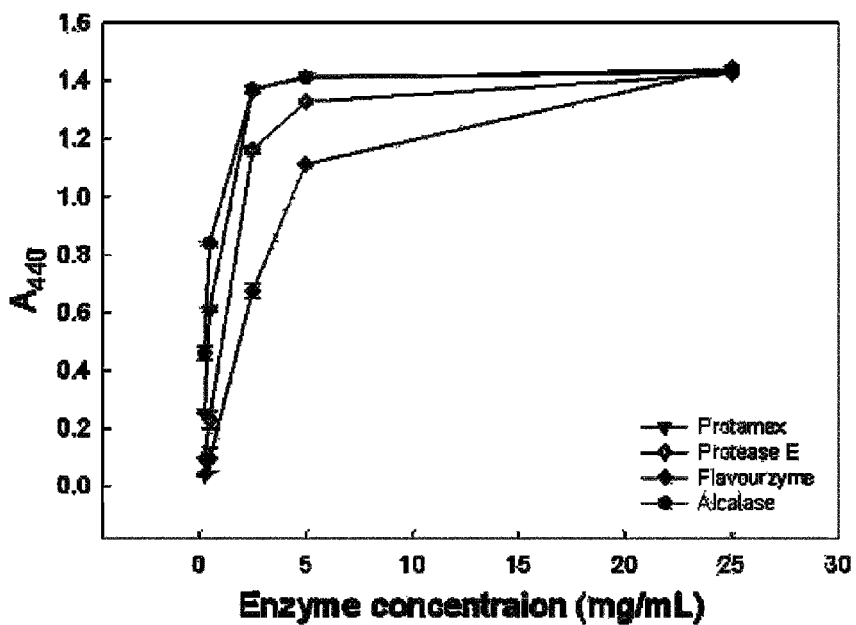
FIG. 6 shows the effects of the concentrations of industrial enzymes on the activity, measured by the azocasein analysis.

The results were illustrated in FIG. 5 and FIG. 6. As a result of measuring the activity change according to the concentration of the enzyme, divided into the catalog enzyme and the industrial enzyme, a pattern in which the enzyme activity was saturated according to the increase of the enzyme concentration, similar with when the substrate was increased was observed. In this case, the important thing to consider when selecting the enzyme concentration is to select the enzyme concentration at the section where the enzyme activity increased, and it was judged that the effect of the high pressure treatment may be properly reflected in the enzyme activity at this enzyme concentration. The enzyme concentrations of the pepsin, α-chymotrypsin, papain (from papaya latex), papain (from *Carica papaya*), bromelain, trypsin acetylated, thermolysin, trypsin, ficin, flavourzyme, Protamex, alcalase and protease E, selected through the said process, were 5, 5, 5, 5, 5, 0.5, 0.1, 0.5, 1, 5, 2.5, 0.5 and 2.5 mg/mL, respectively.

C. Changing on Enzyme Activity Depending on High Pressure Treatment Condition

Figure 7:
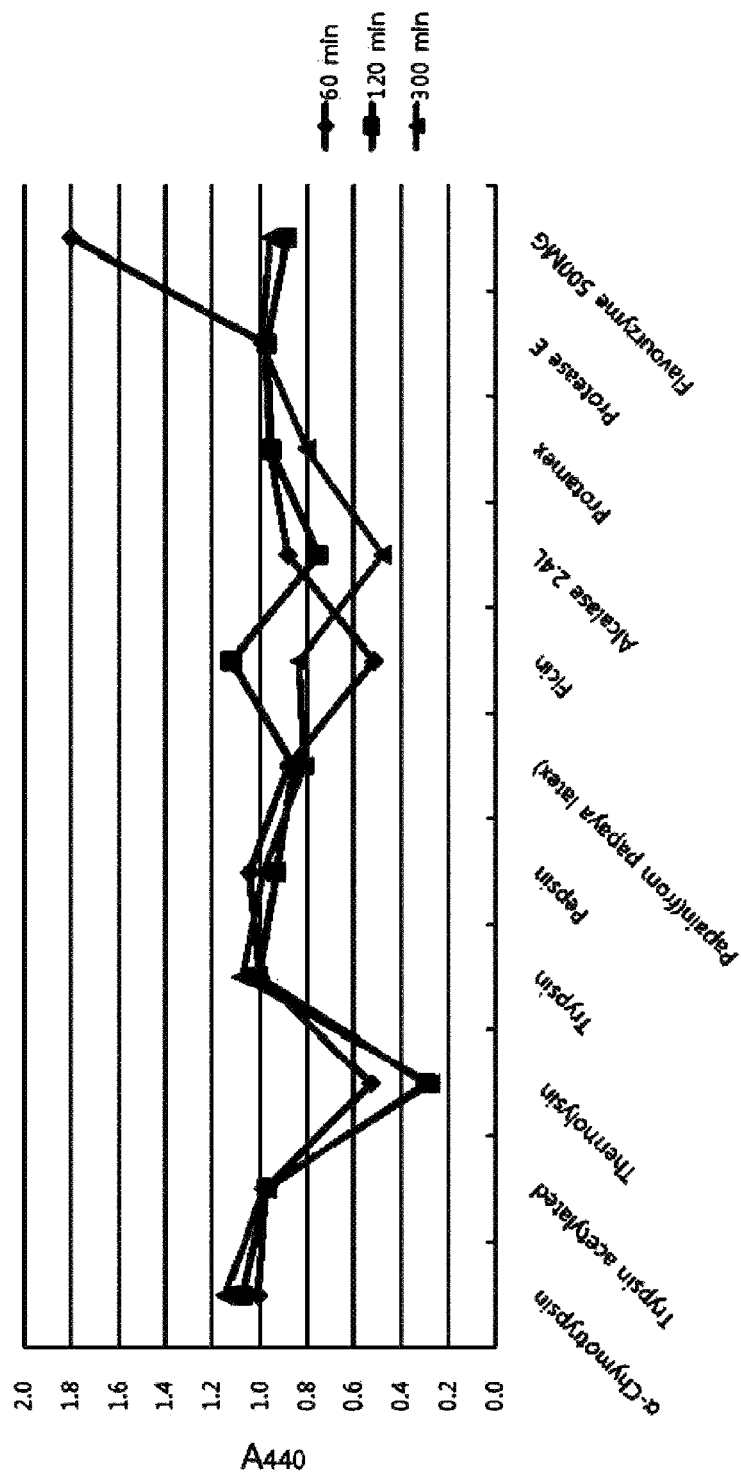
FIG. 7 shows the activities of the enzymes according to the time treated at 100 MPa.
Figure 8:
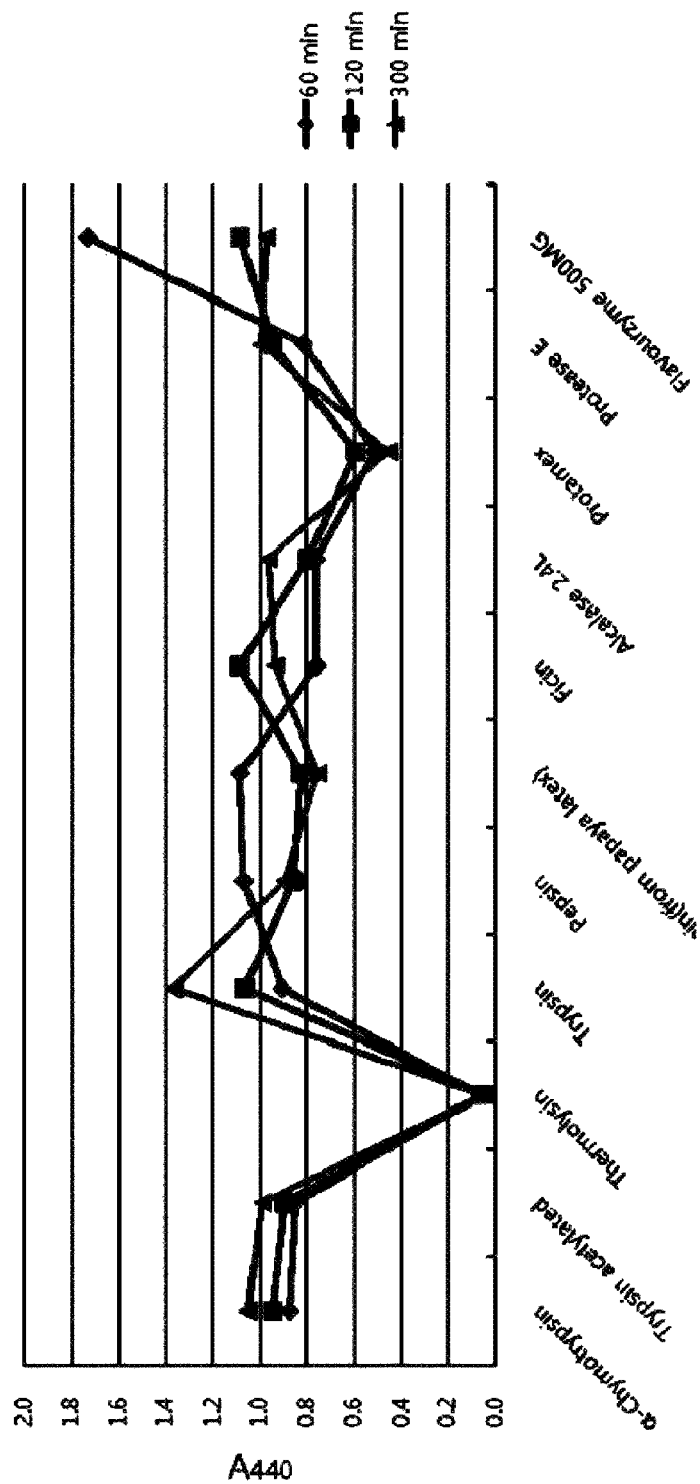
FIG. 8 shows the activities of the enzymes according to the time treated at 300 MPa.

The enzyme activity depending on the high pressure treatment condition was compared with the enzyme activity under the ambient pressure (0.1 MPa) at the enzyme concentration selected in the above experiment. The specific experiment conditions were as listed in Table 2, and the changes on the enzyme activity when treated at 100 and 300 MPa for 60, 120 and 300 min were illustrated in FIG. 7 and FIG. 8, respectively.

The patterns of the enzyme activity were mostly similar at 100 and 300 MPa. However, some of the enzymes showed high pressure-resistance, but other enzymes did not show high pressure-resistance. Representatively, the activity of the trypsin increased even more depending on the time treated at high pressure at 300 MPa while the activity of the thermolysin almost completely disappeared at 300 MPa, thereby showing very weak characteristic on high pressure.

resistance. Accordingly, the present inventors could find that α-chymotrypsin, pepsin, trypsin, trypsin acetylated, flavourzyme, protease E and alcalase had high pressure-resistance.

Figure 11:
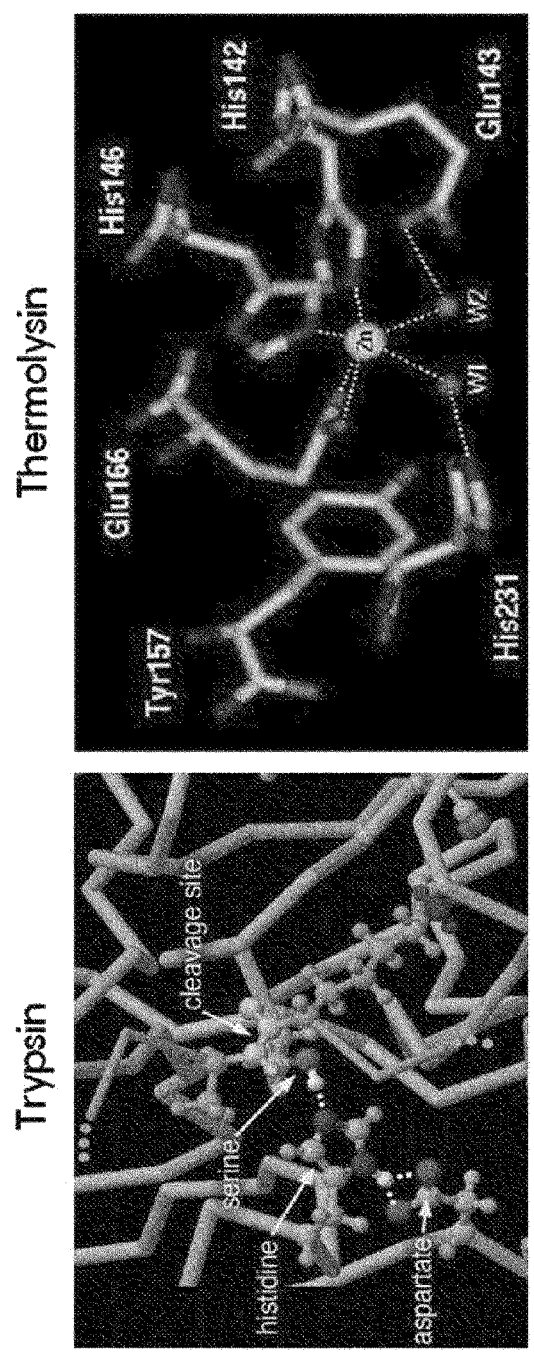
FIG. 11 are pictures comparing active sites of trypsin and thermolysin.
Figure 12:
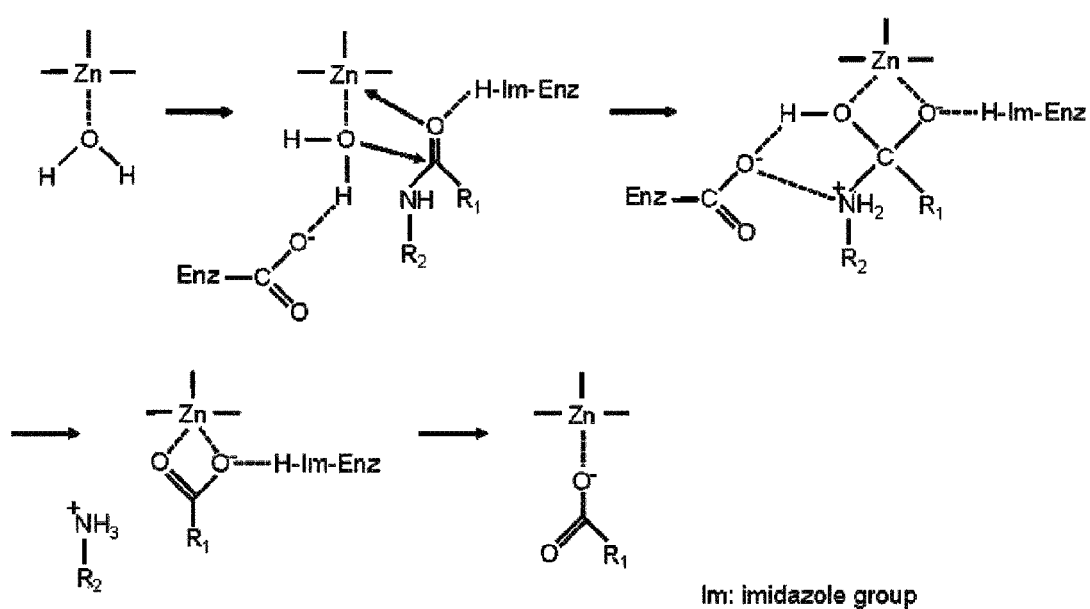
FIG. 12 shows a catalytic mechanism in which the coordinate bondings formed by zinc are destructed depending on the high pressure treatment.

Here, it was determined that the extreme difference between the trypsin and the thermolysin on the pressure-resistance was closely related to mechanisms of the two enzymes (see FIG. 11). When comparing active site structures of these enzymes, it was judged that the active site of the trypsin, one of the serine-based enzymes, was not destructed by the high pressure treatment because there was only covalent bondings. On the contrary, since in the case of the thermolysin, one of the metallic enzymes, wherein a zinc (Zn) ion is bonded to histidine and glutamic acid, amino acids on the active site, by coordinate bondings, also plays an important role in catalytic function of the enzyme (see FIG. 12), it was assumed that the high pressure treatment destructed the coordinate bondings by the zinc, thereby losing the enzyme activity of the thermolysin.

TABLE 2

Design for Test for Treating Various Protein Hydrolysis Enzymes under High Pressure Condition

| Enzyme | Vessel temperature (° C.) | Vessel pressure (MPa) | Reaction time (min) | Enzyme concentration (mg/mL) |
|---|---|---|---|---|
| Pepsin | 37 | 100, 300 | 60, 120, 300 | 5 |
| α-Chymotrypsin | 37 | 100, 300 | 60, 120, 300 | 5 |
| Papain (from *papaya* latex) | 37 | 100, 300 | 60, 120, 300 | 5 |
| Papain (from *Carica papaya*) | 37 | 100, 300 | 60, 120, 300 | 5 |
| Bromelain | 37 | 100, 300 | 60, 120, 300 | 5 |
| Trypsin acetylated | 37 | 100, 300 | 60, 120, 300 | 0.5 |
| Thermolysin | 37 | 100, 300 | 60, 120, 300 | 0.1 |
| Trypsin | 31 | 100, 300 | 60, 120, 300 | 0.5 |
| Ficin | 37 | 100, 300 | 60, 120, 300 | 1 |
| Flavourzyme 500 MG | 37 | 100, 300 | 60, 120, 300 | 5 |
| Protamex | 37 | 100, 300 | 60, 120, 300 | 2.5 |
| Alcalase 2.4L | 37 | 100, 300 | 60, 120, 300 | 0.5 |
| Protease E | 37 | 100, 300 | 60, 120, 300 | 2.5 |

Figure 9:
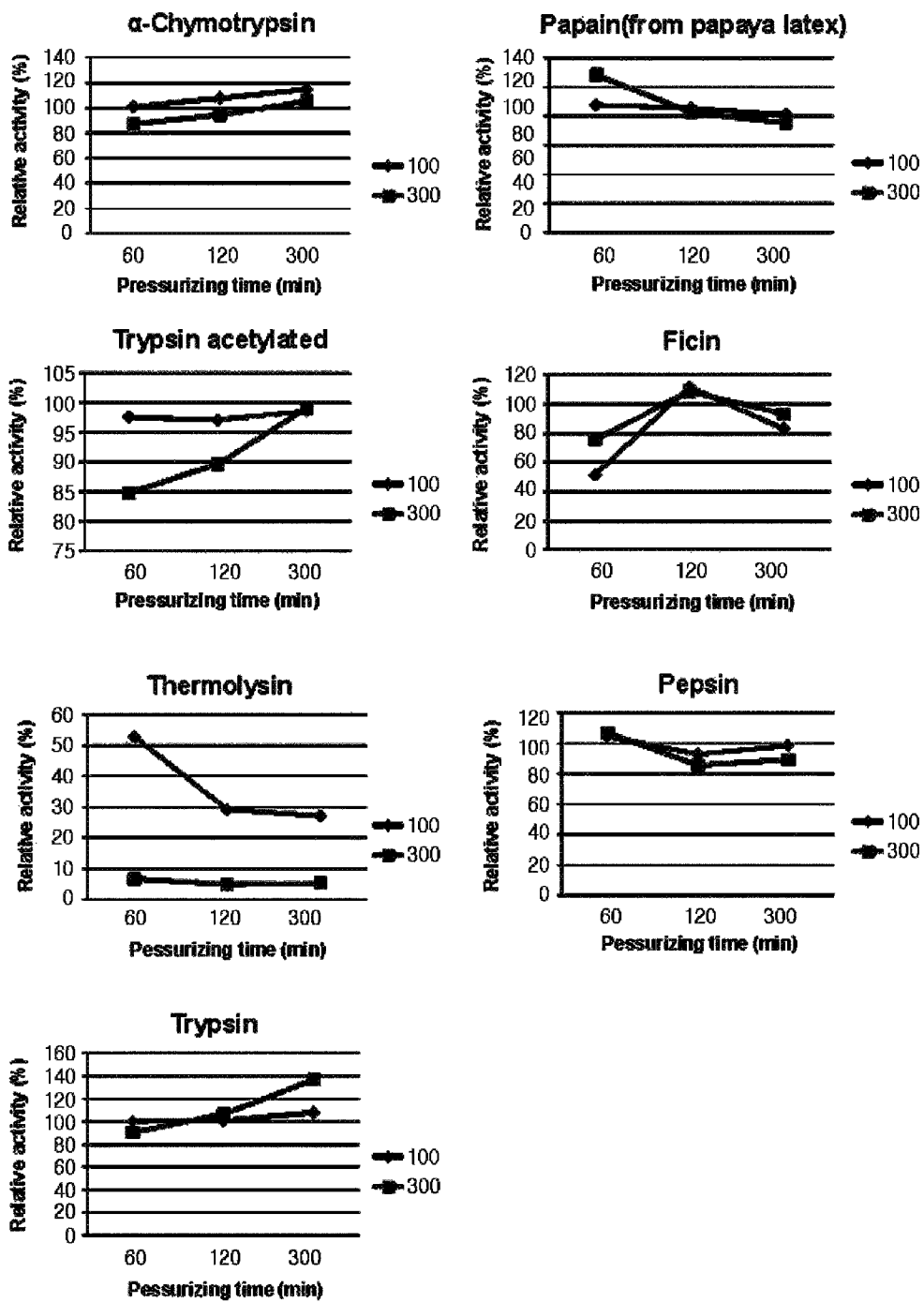
FIG. 9 shows the change on the activity of each catalog hydrolysis enzyme during high pressure treatment.
Figure 10:
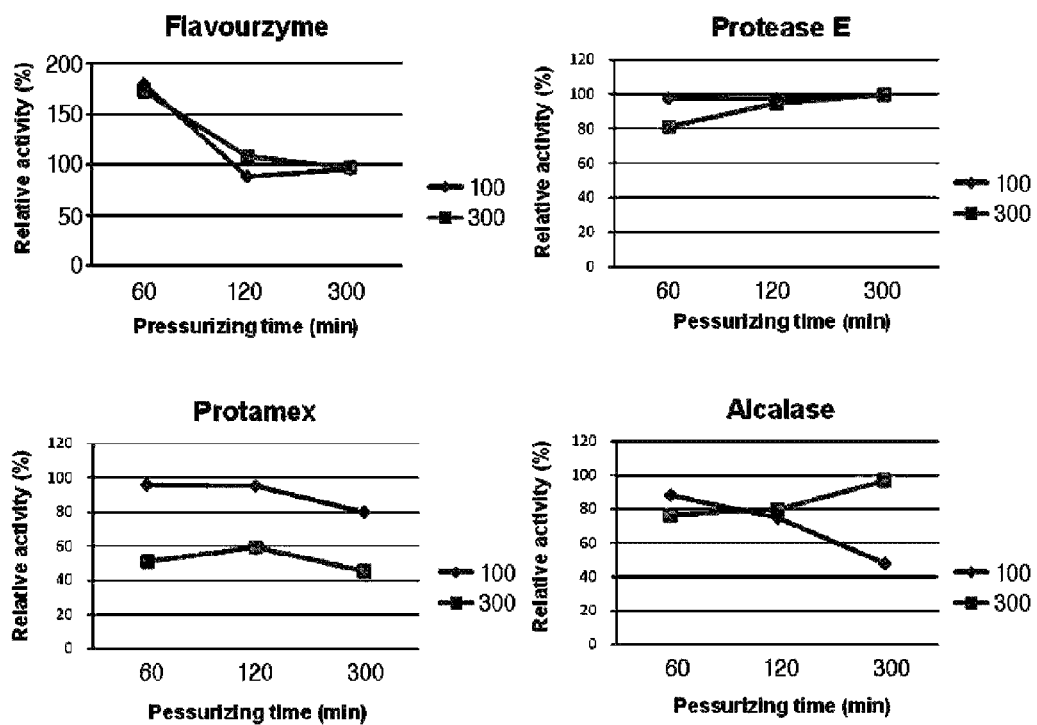
FIG. 10 shows the change on the activity of each industrial hydrolysis enzyme during high pressure treatment.

In order to more clearly investigate the pressure-resistance characteristic of some enzymes, the activities of each enzyme according to the time treated at high pressure at 100 and 300 MPa were expressed as relative activity (%) when regarding the enzyme activity at the ambient pressure as 100, respectively (see FIGS. 9 and 10). Among the catalog enzymes, α-chymotrypsin, pepsin, trypsin and trypsin acetylated were excellent in the pressure-resistance, and trypsin was the most excellent in pressure-resistance as its enzyme activity when treated at 300 MPa for 300 min was 40% higher than when treated at ambient pressure. However, the residual activity of the thermolysin when treated at 300 MPa for 300 min was only 5% or less. Among the industrial enzymes, Protamex was relatively weak on the high pressure treatment, but flavourzyme, protease E and alcalase were excellent in pressure- D. Thermal Inactivation Under High Pressure and Ambient Pressure by Using High Pressure-Resistant Enzyme Among the high pressure-resistant enzymes selected in the above experiment, the trypsin as the catalog enzyme and the protease E as the industrial enzyme were subjected to a time-dependent thermal inactivation test under the ambient pressure and the high pressure, and the heat was treated for 2, 5, 10, 15, 20, 30, 45 and 60 min at each temperature, respectively.

Tables 3 and 4 showed the result of the thermal inactivation test against the trypsin under the high pressure and the ambient pressure. As shown in the following table, it was found that the high pressure treatment largely increased the thermal stability of the enzyme at all temperature conditions.

TABLE 3

Time-Dependent Thermal Inactivation of Trypsin at 300 MPa

| Pressurizing time (min) | Heat treatment (° C.) | | | | |
|---|---|---|---|---|---|
| | 40 | 45 | 50 | 55 | 60 |
| 2 | 1.178 ± 0.054[a] | 1.186 ± 0.015 | 1.150 ± 0.015 | 1.082 ± 0.045 | 0.928 ± 0.008 |
| 5 | 1.238 ± 0.005 | 1.201 ± 0.013 | 1.140 ± 0.023 | 1.090 ± 0.009 | 0.845 ± 0.021 |
| 10 | 1.238 ± 0.004 | 1.200 ± 0.004 | 1.130 ± 0.001 | 1.058 ± 0.016 | 0.749 ± 0.021 |
| 15 | 1.231 ± 0.010 | 1.169 ± 0.015 | 1.137 ± 0.010 | 1.011 ± 0.009 | 0.459 ± 0.022 |
| 20 | 1.204 ± 0.001 | 1.185 ± 0.006 | 1.079 ± 0.032 | 0.944 ± 0.012 | 0.511 ± 0.010 |
| 30 | 1.180 ± 0.011 | 1.148 ± 0.003 | 1.075 ± 0.011 | 0.864 ± 0.011 | 0.366 ± 0.007 |
| 45 | 1.172 ± 0.014 | 1.137 ± 0.005 | 0.974 ± 0.010 | 0.735 ± 0.005 | 0.223 ± 0.011 |
| 60 | 1.162 ± 0.008 | 1.077 ± 0.005 | 0.949 ± 0.012 | 0.699 ± 0.011 | 0.162 ± 0.003 |

[a]Mean ± SD (n = 3).

TABLE 4

Time-Dependent Thermal Inactivation of Trypsin at Ambient Pressure

| Time (min) | Heat treatment (° C.) | | | | |
|---|---|---|---|---|---|
| | 40 | 45 | 50 | 55 | 60 |
| 2 | 1.201 ± 0.067[a] | 1.085 ± 0.025 | 0.683 ± 0.014 | 0.236 ± 0.008 | 0.246 ± 0.008 |
| 5 | 1.237 ± 0.007 | 1.029 ± 0.006 | 0.372 ± 0.010 | 0.420 ± 0.002 | 0.258 ± 0.013 |
| 10 | 1.192 ± 0.026 | 0.907 ± 0.014 | 0.285 ± 0.013 | 0.128 ± 0.010 | 0.106 ± 0.003 |
| 15 | 1.149 ± 0.003 | 0.813 ± 0.003 | 0.446 ± 0.007 | 0.147 ± 0.017 | 0.087 ± 0.000 |
| 20 | 1.129 ± 0.006 | 0.795 ± 0.016 | 0.240 ± 0.015 | 0.125 ± 0.002 | 0.085 ± 0.001 |
| 30 | 1.068 ± 0.002 | 0.778 ± 0.023 | 0.334 ± 0.004 | 0.095 ± 0.009 | 0.076 ± 0.013 |
| 45 | 1.023 ± 0.011 | 0.647 ± 0.005 | 0.113 ± 0.013 | 0.225 ± 0.008 | 0.073 ± 0.005 |
| 60 | 0.949 ± 0.009 | 0.477 ± 0.009 | 0.228 ± 0.009 | 0.067 ± 0.008 | 0.069 ± 0.005 |

[a]Mean ± SD (n = 3).

Figure 13:
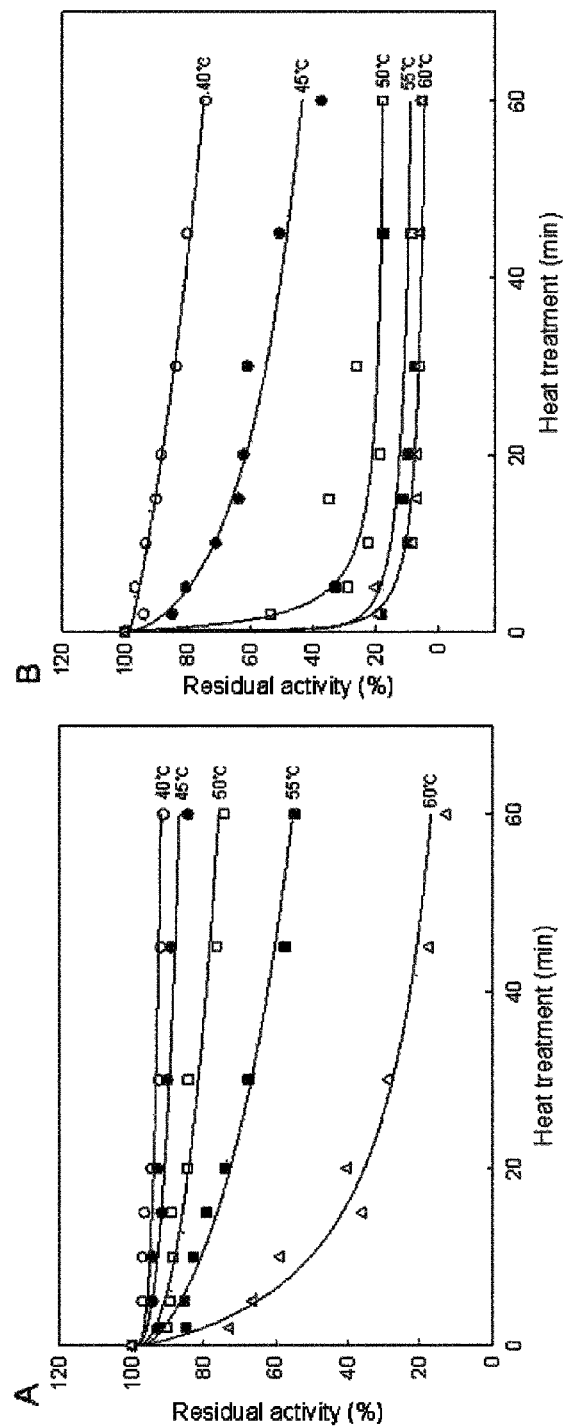
FIG. 13A-B show thermal inactivation profiles of trypsin (○, 40° C.; ●, 45° C.; □, 50° C.; ■, 55° C.; Δ, 60° C.)
Figure 14:
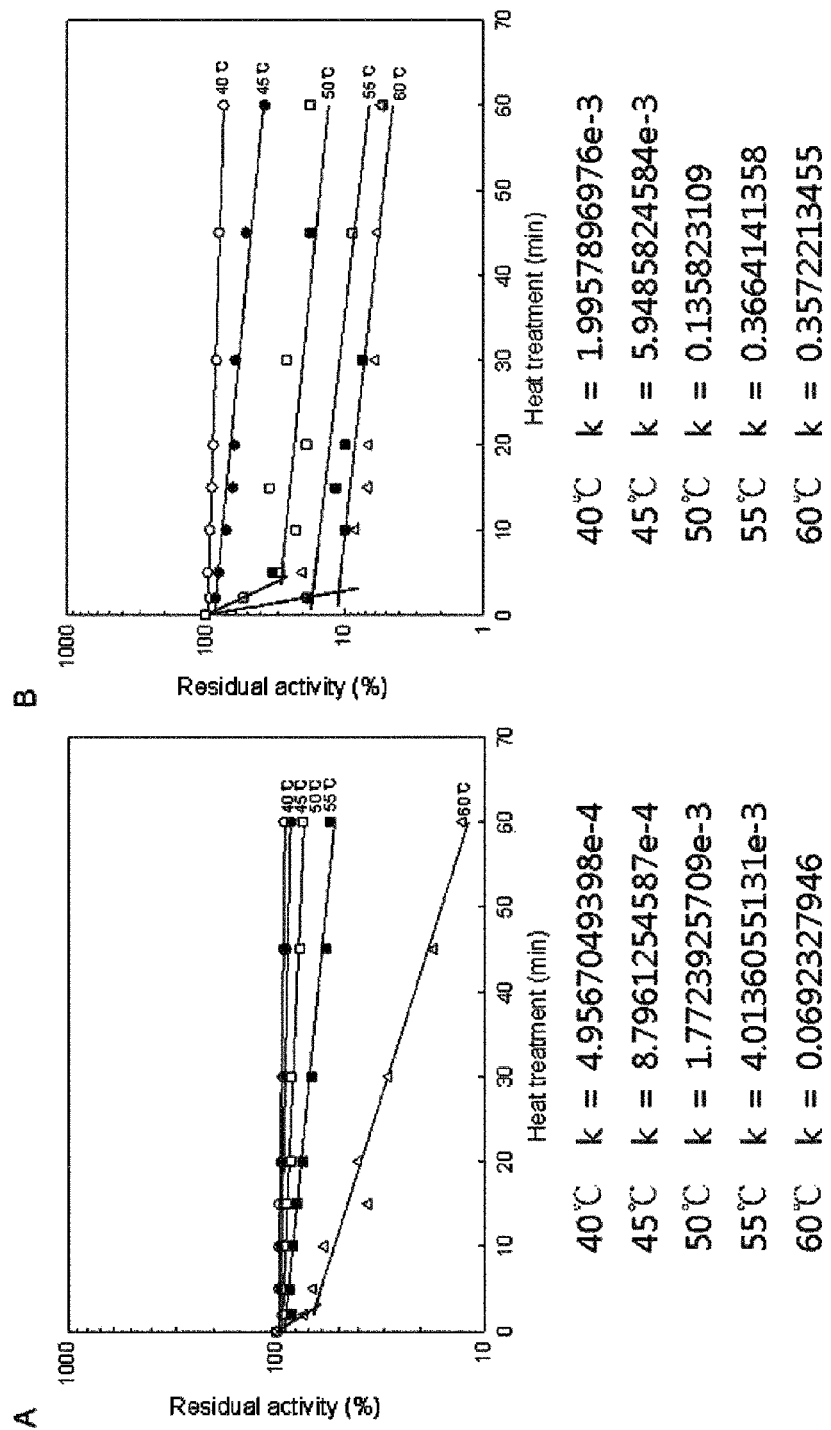
FIG. 14A-B show the result of dynamics analysis of the thermal inactivation profiles of trypsin (○, 40° C.; ●, 45° C.; □, 50° C.; ■, 55° C.; Δ, 60° C.)

When regarding the enzyme activity of the control group measured right after preparing the enzyme solution as 100, the residual activity (%) according to the heat treatment was measured and illustrated in FIG. 13. This result was plotted on as emi-logarithmic scale, and then the rate constant of the first order reaction by the thermal inactivation depending on temperature was calculated (FIG. 14).

The results of the thermal inactivation tests against the protease E under the high pressure and the ambient pressure were expressed in Tables 5 and 6. Like in the case of trypsin, the thermal stability of the enzyme after the high pressure treatment largely increased at all temperature conditions, and the degree of the increase was larger than the case of trypsin.

Figure 15:
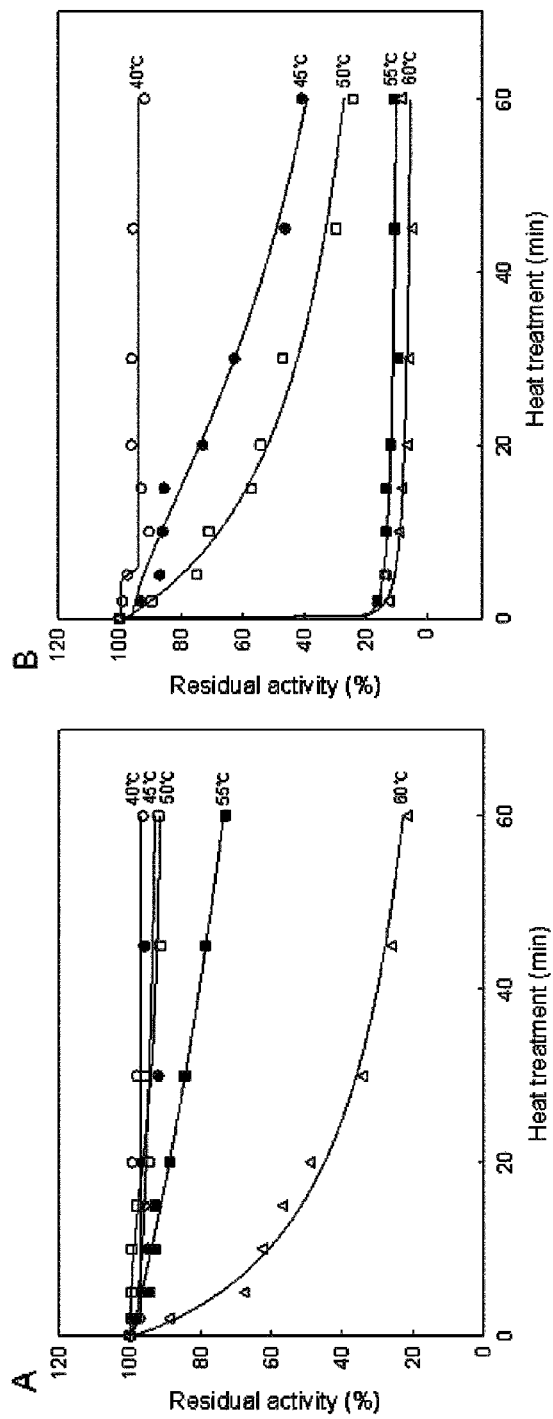
FIG. 15A-B show thermal inactivation profiles of protease E (○, 40° C.; ●, 45° C.; □, 50° C.; ■, 55° C.; Δ, 60° C.)
Figure 16:
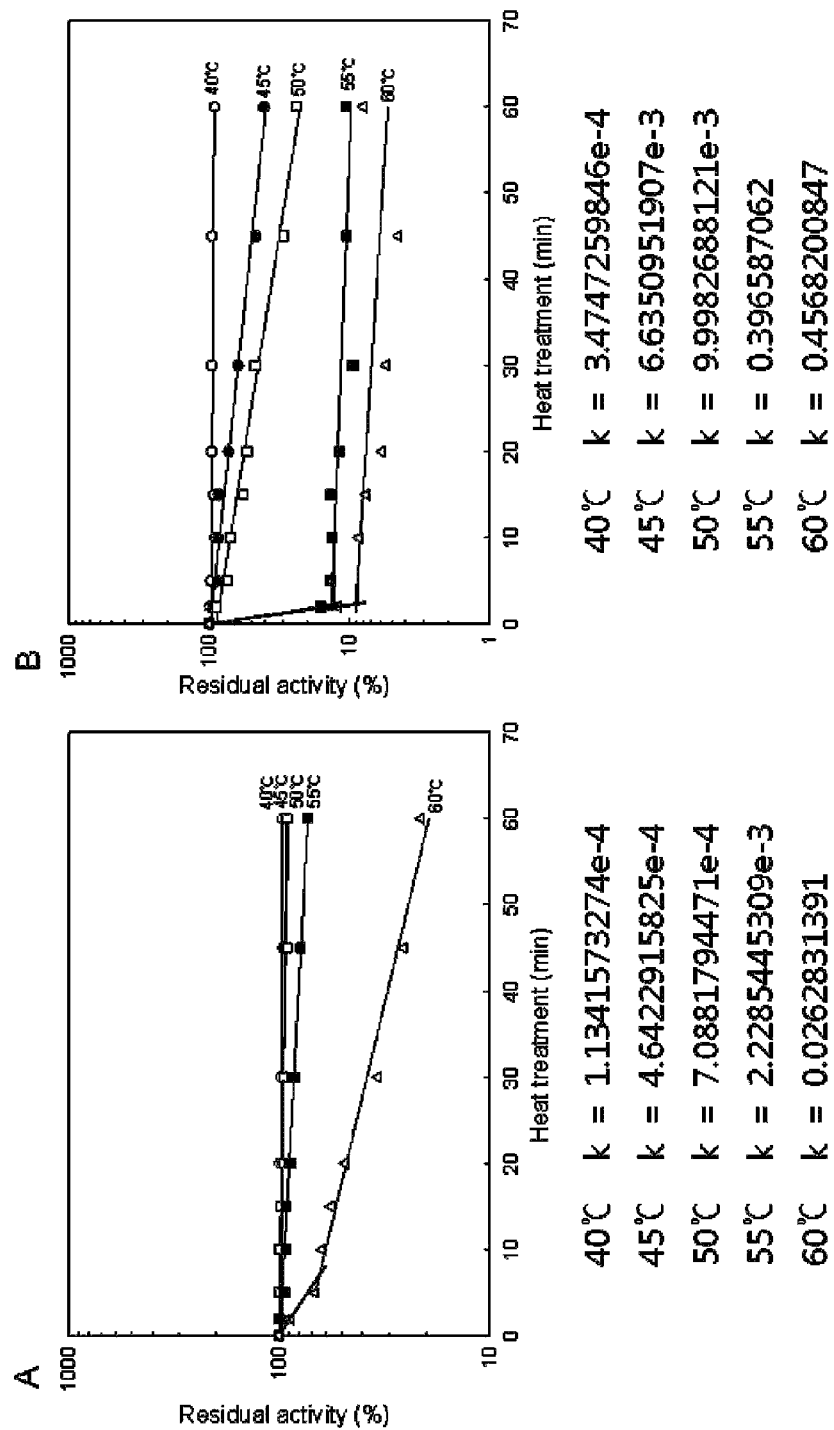
FIG. 16A-B show the result of dynamics analysis of the thermal inactivation profiles of protease E (○, 40° C.; ●, 45° C.; □, 50° C.; ■, 55° C.; Δ, 60° C.)

When regarding the activity of the control group as 100, the residual activity according to the heat treatment was measured and illustrated in FIG. 15. This result was plotted on as emi-logarithmic scale, and then the rate constant of first order reaction by the thermal inactivation depending on temperature was calculated (FIG. 16).

TABLE 5

Time-Dependent Thermal Inactivation of Protease E at 300 MPa

| Pressurizing time (min) | Heat treatment (° C.) | | | | |
|---|---|---|---|---|---|
| | 40 | 45 | 50 | 55 | 60 |
| 2 | 1.252 ± 0.006[a] | 1.263 ± 0.029 | 1.280 ± 0.007 | 1.286 ± 0.020 | 1.141 ± 0.0021 |
| 5 | 1.252 ± 0.016 | 1.259 ± 0.005 | 1.282 ± 0.024 | 1.219 ± 0.026 | 0.865 ± 0.0448 |
| 10 | 1.222 ± 0.015 | 1.223 ± 0.070 | 1.282 ± 0.008 | 1.196 ± 0.028 | 0.800 ± 0.0176 |
| 15 | 1.235 ± 0.011 | 1.254 ± 0.032 | 1.265 ± 0.029 | 1.196 ± 0.002 | 0.726 ± 0.0141 |
| 20 | 1.279 ± 0.019 | 1.242 ± 0.019 | 1.220 ± 0.009 | 1.144 ± 0.024 | 0.627 ± 0.0010 |
| 30 | 1.262 ± 0.020 | 1.183 ± 0.017 | 1.230 ± 0.013 | 1.089 ± 0.032 | 0.437 ± 0.0080 |
| 45 | 1.235 ± 0.004 | 1.232 ± 0.002 | 1.178 ± 0.013 | 1.014 ± 0.004 | 0.328 ± 0.0247 |
| 60 | 1.240 ± 0.008 | 1.186 ± 0.005 | 1.181 ± 0.003 | 0.942 ± 0.022 | 0.271 ± 0.0106 |

[a]Mean ± SD (n = 3).

TABLE 6

Time-Dependent Thermal Inactivation of Protease E at Ambient Pressure

| | Heat treatment (° C.) | | | | |
|---|---|---|---|---|---|
| Time (min) | 40 | 45 | 50 | 55 | 60 |
| 2 | 1.275 ± 0.015[a] | 1.197 ± 0.007 | 1.152 ± 0.034 | 0.207 ± 0.008 | 0.157 ± 0.0053 |
| 5 | 1.256 ± 0.020 | 1.119 ± 0.008 | 0.965 ± 0.044 | 0.176 ± 0.011 | 0.174 ± 0.0028 |
| 10 | 1.164 ± 0.029 | 1.108 ± 0.016 | 0.913 ± 0.017 | 0.173 ± 0.007 | 0.111 ± 0.0017 |
| 15 | 1.196 ± 0.047 | 1.100 ± 0.082 | 0.737 ± 0.007 | 0.174 ± 0.009 | 0.098 ± 0.0040 |
| 20 | 1.237 ± 0.024 | 0.939 ± 0.023 | 0.696 ± 0.008 | 0.154 ± 0.012 | 0.076 ± 0.0068 |
| 30 | 1.235 ± 0.011 | 0.805 ± 0.046 | 0.605 ± 0.031 | 0.123 ± 0.016 | 0.070 ± 0.0047 |
| 45 | 1.229 ± 0.029 | 0.594 ± 0.016 | 0.383 ± 0.019 | 0.135 ± 0.007 | 0.059 ± 0.0018 |
| 60 | 1.182 ± 0.007 | 0.525 ± 0.020 | 0.311 ± 0.014 | 0.137 ± 0.005 | 0.103 ± 0.0028 |

[a]Mean ± SD (n = 3).

Figure 17:
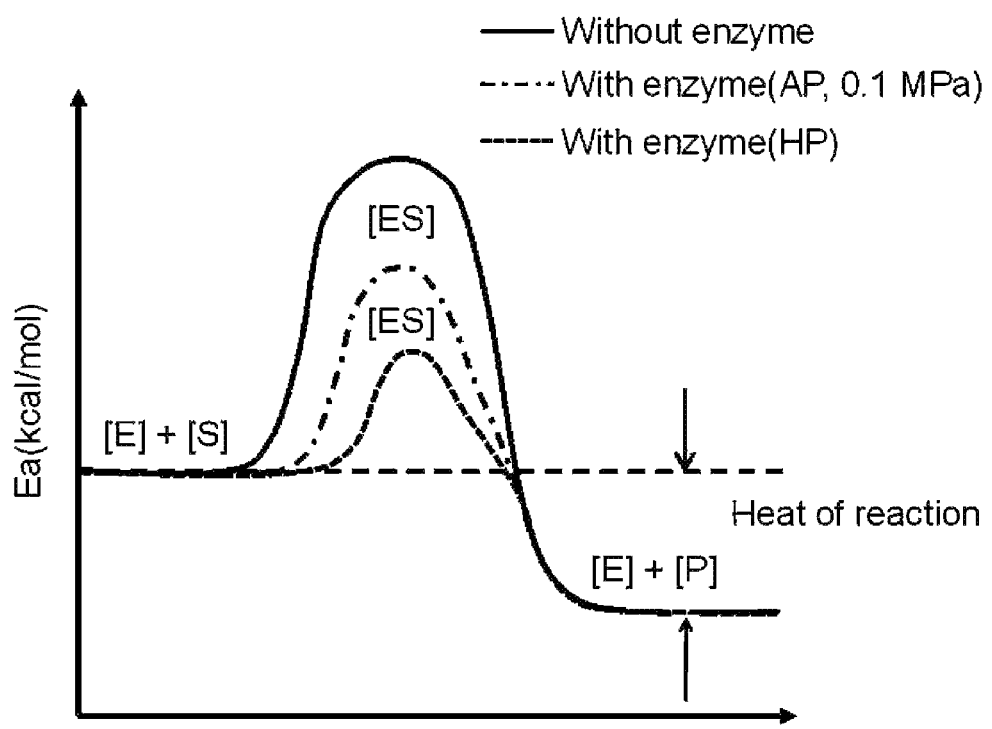
FIG. 17 is a graph comparing a non-enzyme reaction and enzyme reactions under the ambient pressure and at the high pressure.

The result of calculating the activation energy (Ea) from the rate constant of the first order reaction of FIG. 14 and FIG. 16 by Arrhenius plot was shown in Table 7. Activation energies of the trypsin and the protease E at high pressure reaction were 38.9 and 51.5 kcal/mol, and were lower than those of the ambient pressure reaction of 60.2 and 76.5 kcal/mol. Consequently, the high pressure condition increased the reaction rate of the enzyme by lowering the activation energy of the enzyme reaction (see FIG. 17), and it was estimated that this may be expressed as the yield increase of the reaction product.

TABLE 7

First Order Rate Constant of Trypsin and Protease E at 300 MPa and Ambient Pressure

| | | k × 10$^{-2}$ (min$^{-1}$) | | | | | $E_a$ |
|---|---|---|---|---|---|---|---|
| enzyme | | 40° C. | 45° C. | 50° C. | 55° C. | 60° C. | (cal mol$^{-1}$ K$^{-1}$) |
| Trypsin | A | 0.0496 × 10$^{-2}$ | 0.0880 × 10$^{-2}$ | 0.1772 × 10$^{-2}$ | 0.4014 × 10$^{-2}$ | 6.9233 × 10$^{-2}$ | 38993 |
| | B | 0.1996 × 10$^{-2}$ | 0.5949 × 10$^{-2}$ | 13.582 × 10$^{-2}$ | 36.641 × 10$^{-2}$ | 35.722 × 10$^{-2}$ | 60289 |
| Protease | A | 0.0113 × 10$^{-2}$ | 0.0464 × 10$^{-2}$ | 0.0709 × 10$^{-2}$ | 0.2229 × 10$^{-2}$ | 2.6283 × 10$^{-2}$ | 51509 |
| E | B | 0.0347 × 10$^{-2}$ | 0.6635 × 10$^{-2}$ | 0.9998 × 10$^{-2}$ | 39.659 × 10$^{-2}$ | 45.682 × 10$^{-2}$ | 76505 |

A, High pressure treatment; B. ambient pressure treatment.

Example 5

Preparation of Enzyme Hydrolysate Under High Pressure Hydrolysis Condition from Agricultural and Fishery Protein Hydrolysis test for each type of enzymes was conducted as follows by using wheat gluten and anchovy fine powder as a reaction substrate and water as a reaction solvent. The wheat gluten and the anchovy fine powder were dissolved in distilled water to make a 12% solution. The hydrolysis enzyme used herein were alcalase, Protamex, Marugoto E (protease E) and flavourzyme, and of them, one, two, three and four enzymes were combined before treating. As a method for treating the enzyme, in the case of the ambient pressure treatment, the substrate was hydrolyzed with the enzyme in a beaker in a 50° C. water bath for 1 hour, and in the case of the high pressure treatment, the substrate was hydrolyzed with the enzyme in a vinyl pouch at 50° C. and 300 MPa for 1 hour. The thermal inactivation was conducted by heating in a 90° C. water bath for 10 min Centrifugation after the enzyme hydrolysis was conducted at 10000 g and 10° C. for 30 min. The enzyme hydrolysate was electrophoresed, and then suspended solid (SS) was measured by water determination method using sea sand in a 105° C. dry oven. Further, degree of hydrolysis nitrogen (DHN) was measured by measuring nitrogen content against a TCA-soluble fraction and a total soluble fraction of hydrolysates, and a 12% sample suspension not treated with any enzyme by Kjeldahlanalysis.

A. Result of Electrophoresis Pattern of Enzyme Hydrolysate

Figure 18:
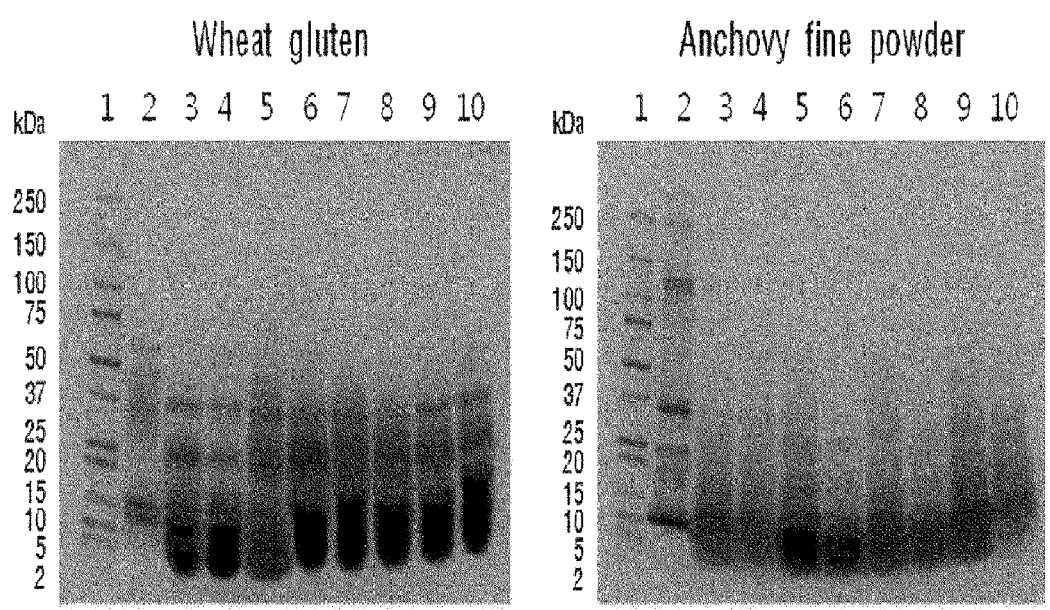
FIG. 18 shows electrophoresis patterns of enzyme hydrolysates according to treatment with one enzyme (1, markers; 2, non-enzyme treated 12% protein (AP); 3, F (AP); 4, F (HP); 5, A (AP); 6, A (HP); 7, P (AP); 8, P (HP); 9, M (AP); 10, M (HP); AP, ambient pressure; HP, 300 MPa. F, flavourzyme; A, alcalase; P, Protamex; M, MarugotoE)
Figure 19:
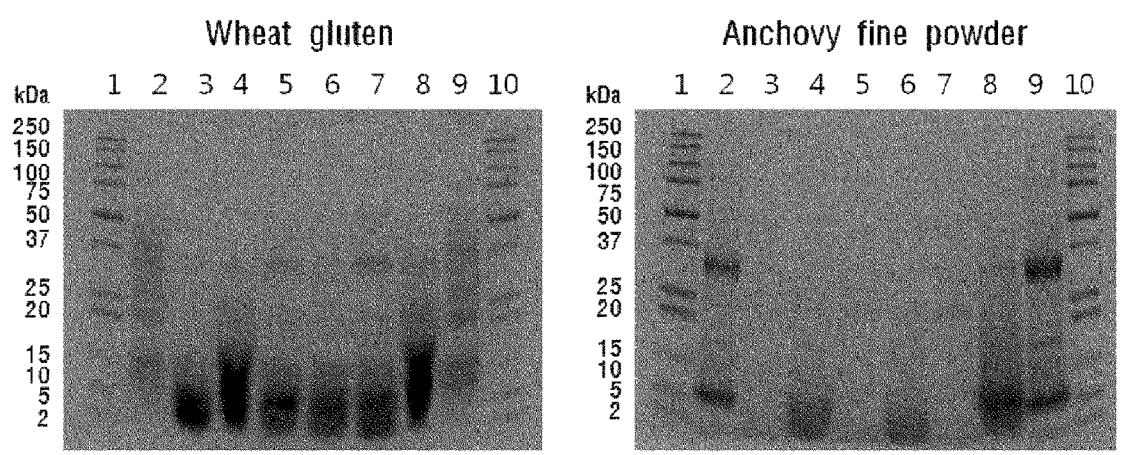
FIG. 19 shows electrophoresis patterns of enzyme hydrolysates according to treatment with two enzymes (1,10, markers; 2, non-enzyme treated 12% protein (AP); 3, FA (AP); 4, FA (HP); 5, FP (AP); 6, FP (HP); 7, FM (AP); 8, FM (HP); 9, 12% non-enzyme treated 12% protein; AP, ambient pressure; HP, 300 MPa; F, flavourzyme; A, alcalase; P, Protamex; M, Marugoto E)
Figure 20:
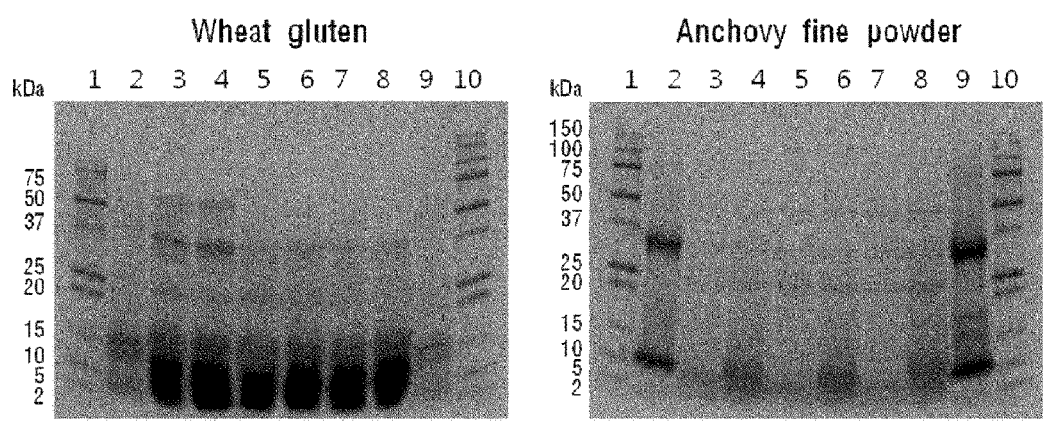
FIG. 20 shows electrophoresis patterns of enzyme hydrolysates according to treatment with three enzymes (1,10, markers; 2, non-enzyme treated 12% protein (AP); 3, FAP (AP); 4, FAP (HP); 5, FAM (AP); 6, FAM (HP); 7, FPM (AP); 8, FPM (HP); 9, non-enzyme treated 12% protein (HP); AP, ambient pressure; HP, 300 MPa; F, flavourzyme; A, alcalase; P, Protamex; M, Marugoto E)
Figure 21:
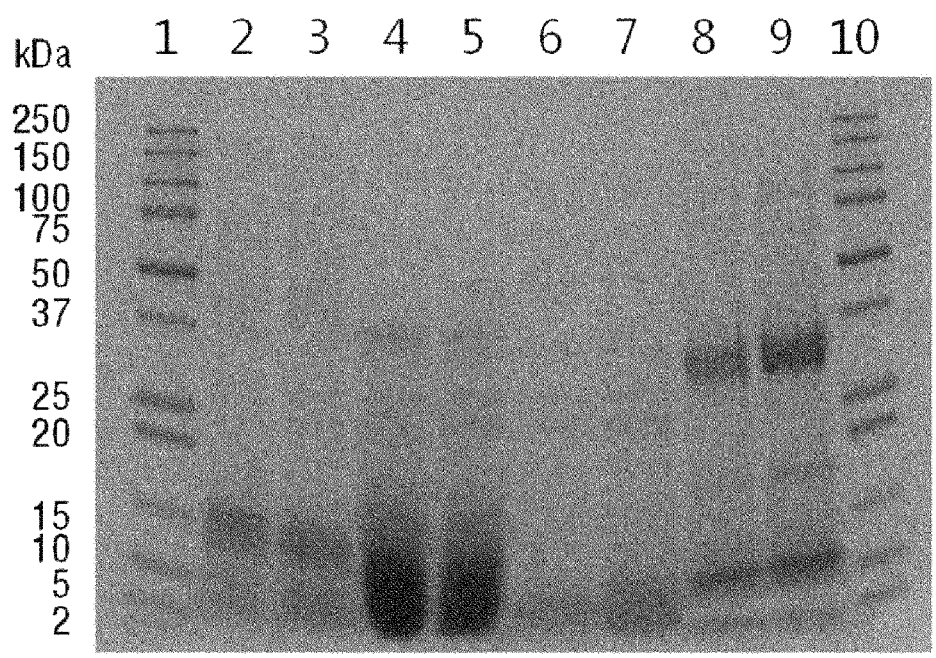
FIG. 21 shows an electrophoresis pattern of enzyme hydrolysates according to treatment with four enzymes (1,10, markers; 2, non-enzyme treated 12% wheat gluten (AP); 3, non-enzyme treated 12% wheat gluten (HP); 4, WG (AP); 5, WG (HP); 6, AFP (AP); 7, AFP (HP); 8, non-enzyme treated 12% anchovy fine powder (AP); 9, non-enzyme treated 12% anchovy fine powder (HP); AP, ambient pressure; HP, 300 MPa; F, flavourzyme; A, alcalase; P, Protamex; M, Marugoto E)
Figure 22:
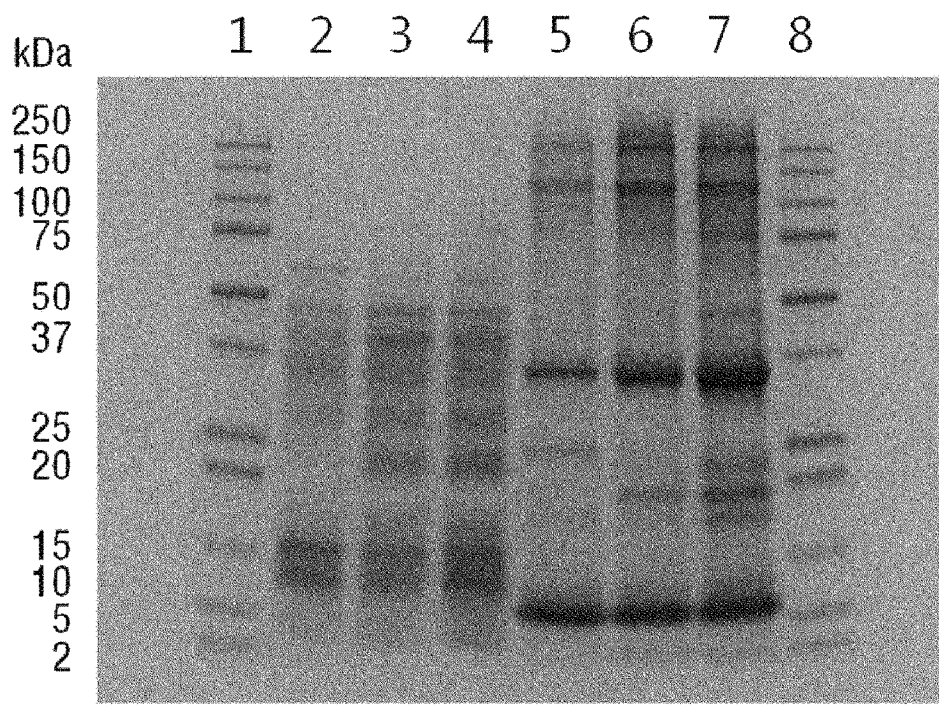
FIG. 22 shows an electrophoresis pattern in the case of not treating any enzyme (1,8, marker; 2, 12% WG; 3, 12% WG (AP); 4, 12% WG (HP); 5, 12% AFP; 6, 12% AFP (AP); 7, 12% AFP (HP); AP, ambient pressure; HP, 300 MPa; F, flavourzyme; A, alcalase; P, Protamex; M, Marugoto E)

Electrophoresis pattern of the enzyme hydrolysate obtained from the hydrolysis test conducted by the above process was examined. As the result, when comparing bands of the case treated with one enzyme (FIG. 18), the case treated with two enzymes (FIG. 19), the case treated with three enzymes (FIG. 20) and the case treated with four enzymes (FIG. 21), and the case not treated with any enzyme (FIG. 22), it was confirmed that the hydrolysates treated with the enzymes showed more band patterns of molecular weight of thousands or less than the case not treated with any enzyme.

Figure 23:
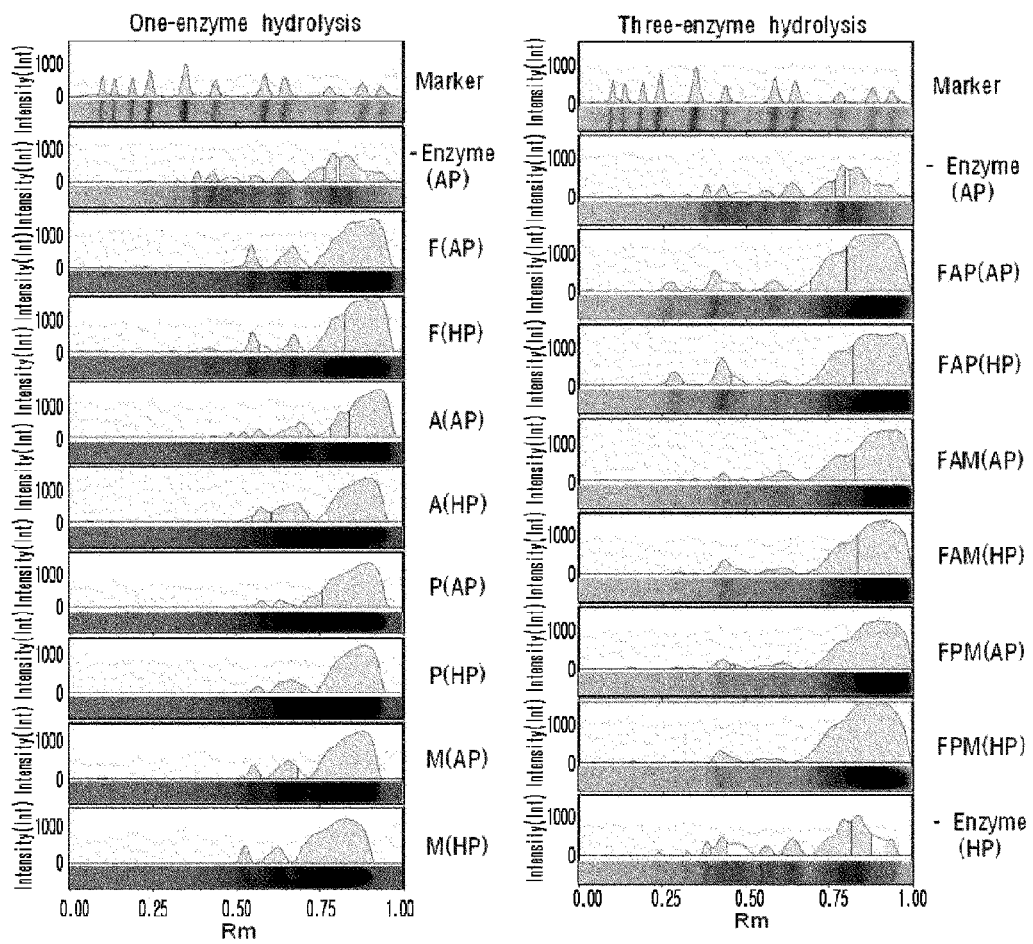
FIG. 23 shows electrophoregrams of the enzyme hydrolysates of the wheat gluten (AP, ambient pressure; HP, 300 MPa)

An electrophoregram was drawn from the electrophoresis patterns of the enzyme hydrolysates obtained from the cases treating one enzyme and three enzymes to the wheat gluten (FIG. 23). It was confirmed that there was little difference according to enzyme treating groups, but when compared with the group not treated with any enzyme, the effect of the changes on the electrophoregrams by hydrolysis was obvious.

Figure 24:
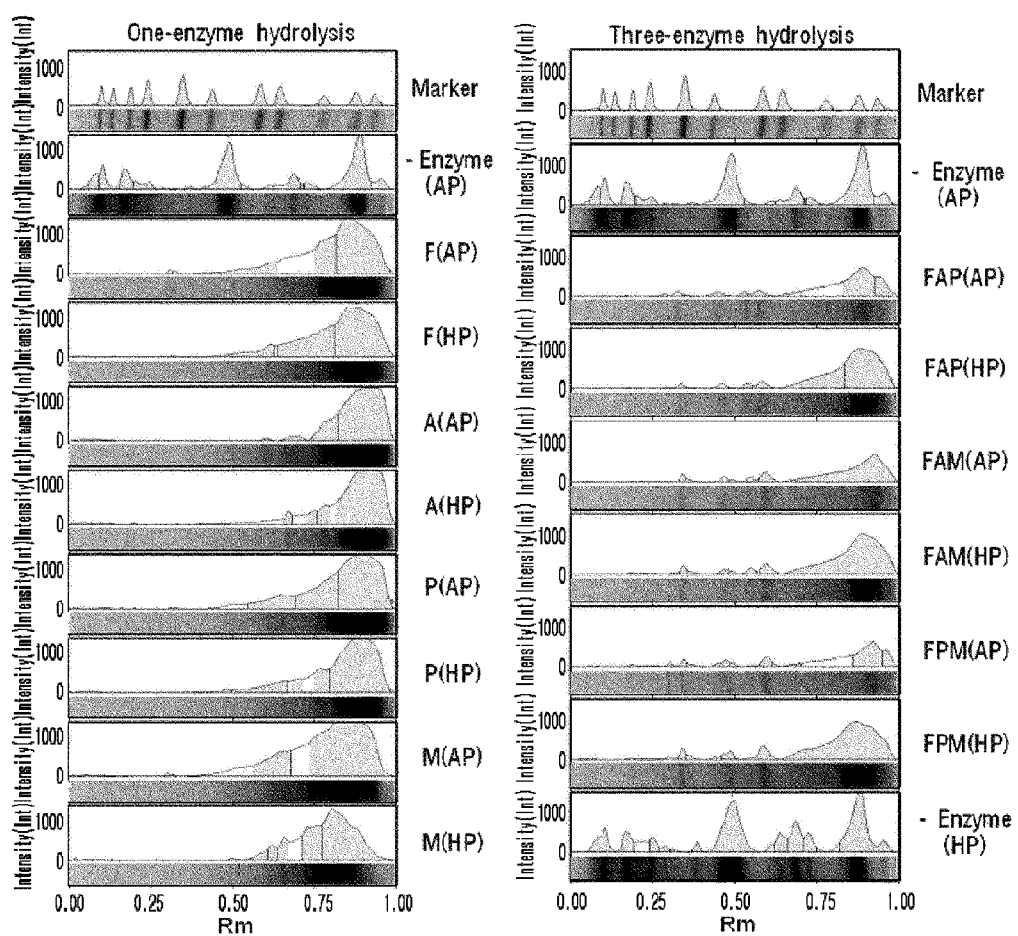
FIG. 24 shows electrophoregrams of the enzyme hydrolysates of the anchovy fine powder (AP, ambient pressure; HP, 300 MPa)
Figure 25:
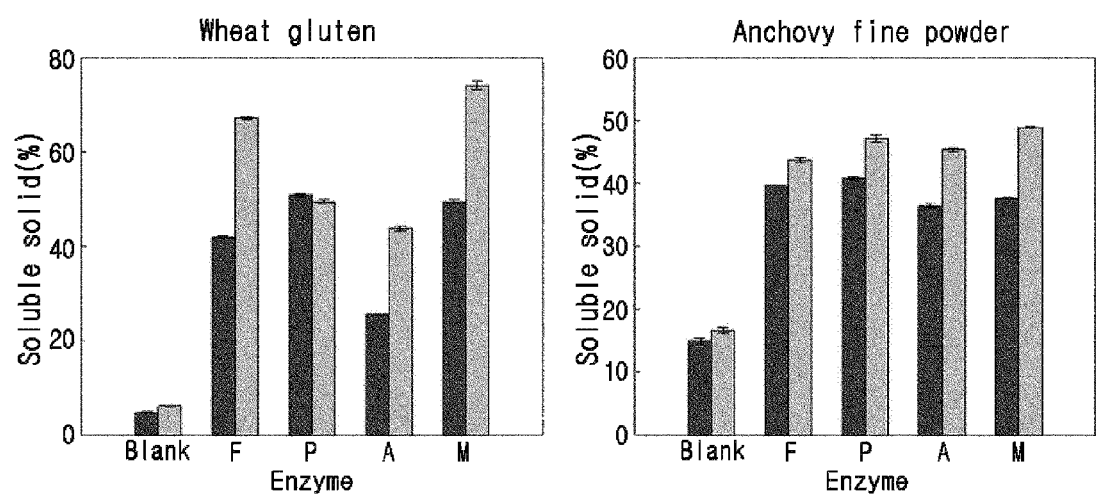
FIG. 25 shows the results of measuring the soluble solids of the enzyme hydrolysates according to the treatment with one enzyme.
Figure 26:
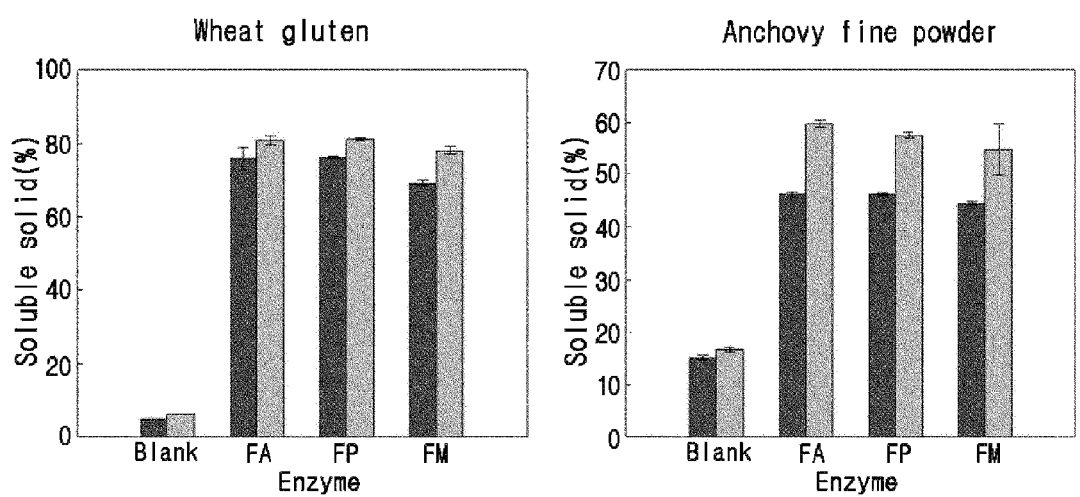
FIG. 26 shows the results of measuring the soluble solids of the enzyme hydrolysates according to the treatment with two enzymes.
Figure 27:
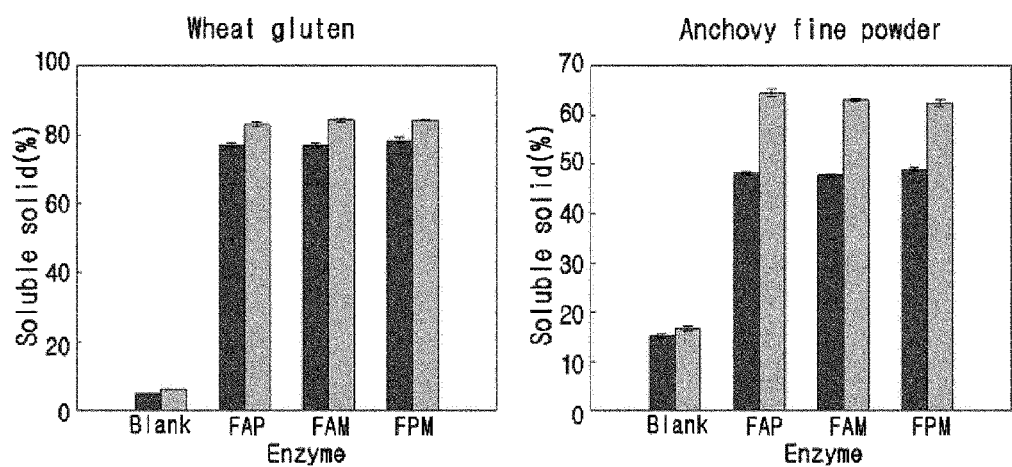
FIG. 27 shows the results of measuring the soluble solids of the enzyme hydrolysates according to the treatment with three enzymes.
Figure 28:
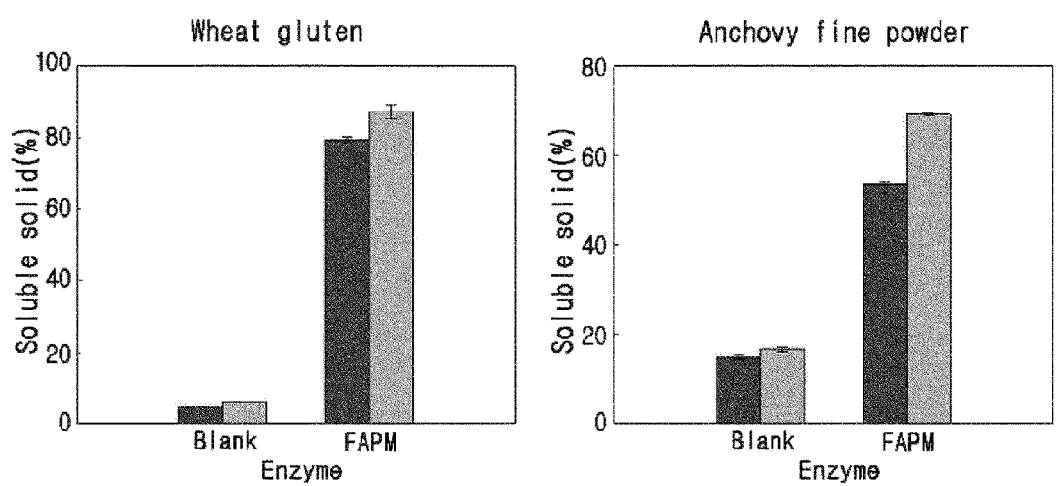
FIG. 28 shows the results of measuring the soluble solids of the enzyme hydrolysates according to the treatment with four enzymes.

The electrophoregram of the anchovy fine powder showed a similar pattern with the result of the wheat gluten (FIG. 24).

B. Result of Measuring Soluble Solid (SS) of Enzyme Hydrolysate

Results of measuring the soluble solid (SS) of the enzyme hydrolysates treated with one enzyme, two enzymes, three enzymes and four enzymes by the 105° C. drying method using sea sand were shown in Table 8. The SS was higher in the case of four enzymes than the case of one enzyme, and at the high pressure than at the ambient pressure, and there from, it was concluded that the enzyme was hydrolyzed better as the number of the enzyme used for the enzyme hydrolysis increased, and at high pressure condition.

TABLE 8

| | Wheat gluten | | Anchovy fine powder | |
|---|---|---|---|---|
| Enzyme | AP (%)[a] | HP (%)[b] | AP (%) | HP (%) |
| F | 42.00 ± 0.18 | 67.23 ± 0.24 | 39.66 ± 0.05 | 43.70 ± 0.31 |
| P | 50.85 ± 0.36 | 49.43 ± 0.33 | 40.75 ± 0.23 | 47.12 ± 0.56 |
| A | 25.58 ± 0.21 | 43.61 ± 0.50 | 36.44 ± 0.33 | 45.33 ± 0.36 |
| M | 49.48 ± 0.38 | 74.08 ± 0.84 | 37.62 ± 0.06 | 48.89 ± 0.13 |
| FA | 75.78 ± 3.15 | 80.84 ± 1.15 | 46.27 ± 0.35 | 59.63 ± 0.69 |
| FP | 76.06 ± 0.36 | 81.06 ± 0.27 | 46.17 ± 0.22 | 57.54 ± 0.58 |
| FM | 69.10 ± 0.88 | 78.05 ± 1.15 | 44.57 ± 0.26 | 54.80 ± 4.97 |
| FAP | 77.10 ± 0.68 | 83.04 ± 0.63 | 48.26 ± 0.31 | 64.51 ± 0.84 |
| FAM | 76.84 ± 0.65 | 84.32 ± 0.45 | 47.74 ± 0.29 | 63.01 ± 0.22 |
| FPM | 78.29 ± 0.79 | 84.19 ± 0.26 | 49.06 ± 0.38 | 62.40 ± 0.60 |
| FAPM | 79.37 ± 0.90 | 87.23 ± 1.97 | 53.74 ± 0.31 | 69.23 ± 0.28 |

[a]Treatment at ambient pressure.
[b]Treatment at 300 MPa.
F. Flavourzyme;
P. Protamex;
A. Alcalase;
M. Marugoto E.

The relationship in Table 8 was expressed in graphs of FIGS. 25 to 28, and they visually show the relationship between the SS content and the enzyme hydrolysis under the high pressure and the ambient pressure conditions.

C. Result of Measuring Degree of Hydrolysis Nitrogen (DHN) of Enzyme Hydrolysate Results of measuring the degree of hydrolysis nitrogen (DHN) of the hydrolysate hydrolyzed by the protease were shown in Table 9 and Table 10. The DHN is used as one of the standards for the ratio of the number of hydrolyzed peptide bonds to the total number of the peptide bonds, and as the result of measuring the SS, the DHN and the solubility were higher as the number of the treated enzyme was increased and the enzyme hydrolysis was conducted under the high pressure condition than at the ambient pressure because the number of the hydrolyzed peptide was more. When compared with the value of the Blank, it could be found that the effect of the hydrolysis was higher as the number of the treated enzyme increased. The result of treating under the ambient pressure was shown in Table 9, and the result of treating under the high pressure (300 MPa) was shown in Table 10.

TABLE 9

| | Wheat gluten | | | | Anchovy fine powder | | | |
|---|---|---|---|---|---|---|---|---|
| Enzyme | Total soluble-N (%) | TCA-soluble-N (%) | Solubility (%) | DHN (%) | Total soluble-N (%) | TCA-soluble-N (%) | Solubility (%) | DHN (%) |
| Blank[a] | 0.27 ± 0.04 | 0.19 ± 0.01 | 2.52 | 1.77 | 0.91 ± 0.02 | 0.71 ± 0.02 | 12.08 | 9.43 |
| F | 3.77 ± 0.08 | 2.54 ± 0.01 | 35.14 | 23.67 | 2.46 ± 0.04 | 2.43 ± 0.01 | 32.67 | 32.27 |
| FA | 6.18 ± 0.38 | 3.02 ± 0.04 | 57.60 | 28.15 | 3.25 ± 0.05 | 3.17 ± 0.07 | 43.16 | 42.10 |
| FAM | 7.14 ± 0.21 | 6.82 ± 0.07 | 66.54 | 63.56 | 3.24 ± 0.13 | 2.77 ± 0.01 | 43.03 | 36.79 |
| FAMP | 7.14 ± 0.23 | 6.87 ± 0.08 | 66.54 | 64.03 | 3.65 ± 0.13 | 3.58 ± 0.11 | 48.47 | 47.54 |

[a]Without enzyme treatment.
Tatal-N = Wheat gluten, 10.73 ± 0.07%: Anchovy fine powder, 7.53 ± 0.02%.
DHN (%) = TCA-soluble-N/Tatal-N * 100

TABLE 10

| | Wheat gluten | | | | Anchovy fine powder | | | |
|---|---|---|---|---|---|---|---|---|
| Enzyme | Total soluble-N (%) | TCA-soluble-N (%) | Solubility (%) | DHN (%) | Total soluble-N (%) | TCA-soluble-N (%) | Solubility (%) | DHN (%) |
| Blank[a] | 0.35 ± 0.02 | 0.32 ± 0.02 | 3.26 | 2.98 | 0.98 ± 0.03 | 0.78 ± 0.02 | 13.01 | 10.36 |
| F | 6.25 ± 0.28 | 5.77 ± 0.07 | 58.25 | 53.77 | 3.56 ± 0.07 | 3.51 ± 0.04 | 47.28 | 46.61 |
| FA | 6.79 ± 0.18 | 6.4 ± 0.1 | 63.28 | 59.65 | 4.15 ± 0.1 | 4.14 ± 0.02 | 55.11 | 54.98 |
| FAM | 7.69 ± 0.14 | 7.53 ± 0.79 | 71.67 | 70.18 | 4.43 ± 0.15 | 4.3 ± 0.02 | 58.83 | 57.10 |
| FAMP | 8.09 ± 0.12 | 7.73 ± 0.1 | 75.40 | 72.04 | 4.87 ± 0.09 | 4.7 ± 0.06 | 64.67 | 62.42 |

[a]Without enzyme treatment.
Tatal-N = Wheat gluten, 10.73 ± 0.07%; Anchovy fine powder, 7.53 ± 0.02%.
DHN (%) = TCA-soluble-N/Tatal-N * 100

Figure 29:
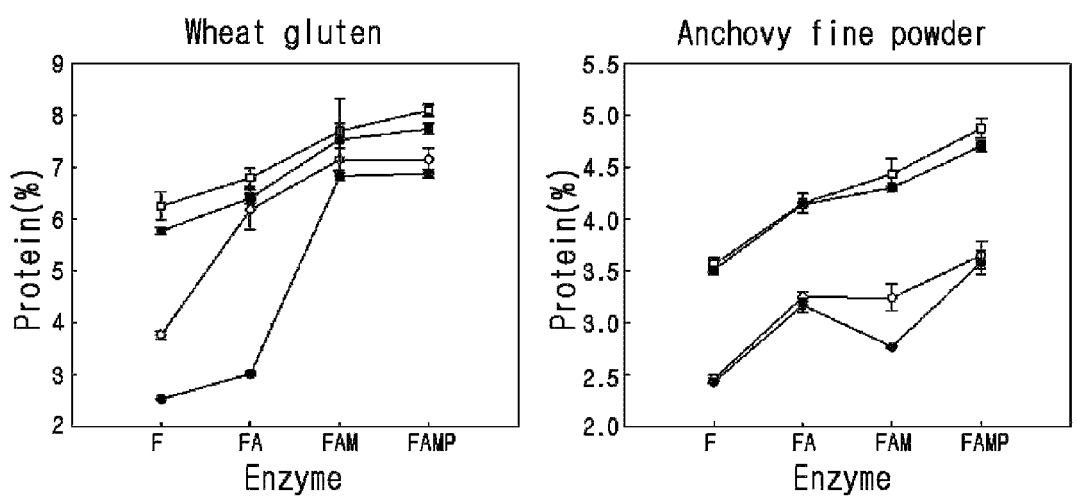
FIG. 29 are results of measuring soluble nitrogen contents of the enzyme hydrolytes of the wheat gluten and the anchovy fine powder (o, Total soluble N (AP); ●, TCA soluble N (AP); □, Total soluble N (HP); ■, TCA soluble N (HP); AP, ambient pressure; HP, 300 MPa)
Figure 30:
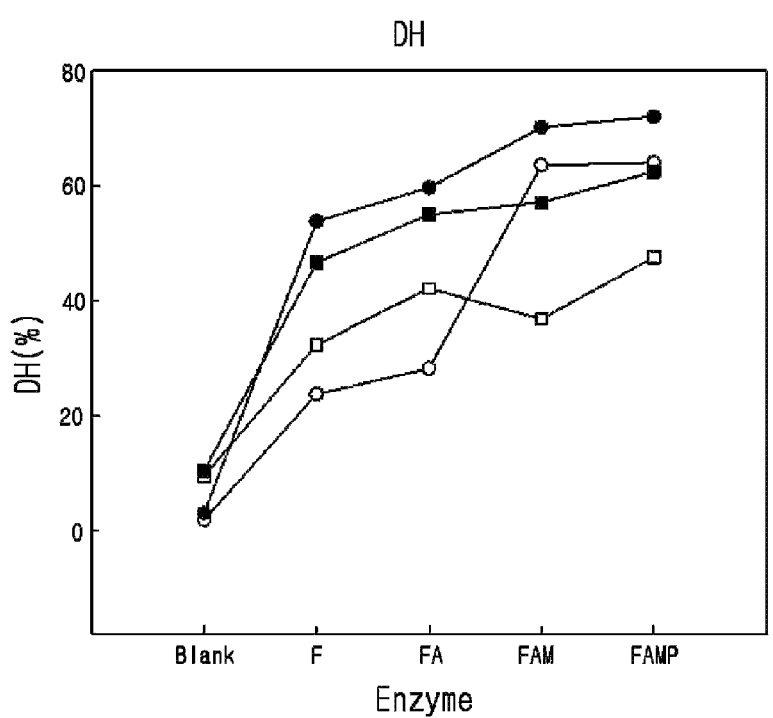
FIG. 30 shows DHN of the enzyme hydrolysates of the wheat gluten and the anchovy fine powder (○, wheat gluten (AP); ●, wheat gluten (HP); □, anchovy fine powder (AP); ■, anchovy fine powder (HP); AP, ambient pressure; HP, 300 MPa)
Figure 31:
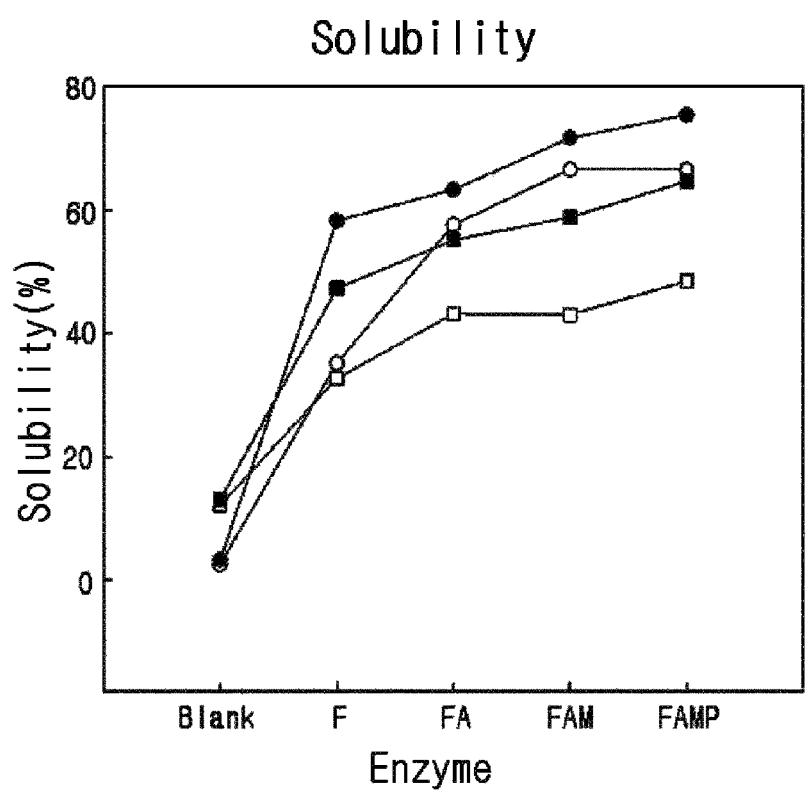
FIG. 31 shows the solubility of the enzyme hydrolysates of the wheat gluten and the anchovy fine powder (○, wheat gluten (AP); ●, wheat gluten (HP); □, anchovy fine powder (AP); ■, anchovy fine powder (HP); AP, ambient pressure; HP, 300 MPa.

The relationship in Table 9 and Table 10 were expressed in graphs of FIGS. 29 to 31, and they visually show the relationship between the enzyme hydrolysis, and the DHN and the solubility under the high pressure and the ambient pressure conditions well.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method for hydrolyzing proteins comprising the steps of:
   a. dissolving a substance in water
   b. combining one or more enzymes selected from the group consisting of pepsin, trypsin trypsin acetylated, flavourzyme, protease E and alcalse
   c. hydrolyzing the substance with the enzyme mixture under a pressure of 100 to 400 MPa maintained for 60 to 300 min.

2. The method according to claim 1, further comprising a heating step wherein the heating is conducted at 40° C. or higher for 2 min or longer.

3. The method according to claim 2, wherein the hydrolyzing step and the heating step are conducted at the same time.

4. A container for hydrolyzing proteins according to the method of claim 1.

5. A method for measuring the activity of an enzyme, which comprises a step of decomposing an azocasein solution, serving as a substrate, by using the enzyme, which is at least one selected from the group consisting of pepsin, trypsin, trypsin acetylated, flavourzyme, protease E and alcalase, and treated under a pressure of 100 to 400 MPa maintained for 60 to 300 min.

6. The method according to claim 5, wherein the concentration of the azocasein is 2 to 5%.

7. The method according to claim 2, wherein the heating step is performed sequentially following the hydrolyzing step.

8. The method according to claim 1, wherein the hydrolyzing step is conducted at a pressure of 300 to 400 MPa.

9. The method according to claim 1, wherein the hydrolyzing step is conducted at a pressure of 300 MPa.

10. The method according to claim 1, further comprising a thermal inactivation step following the hydrolyzing step, wherein the thermal inactivation step comprises heating to 90° C. for 10 minutes.

11. The method according to claim 2, further comprising a thermal inactivation step following the hydrolyzing step, wherein the thermal inactivation step comprises heating to 90° C. for 10 minutes.

12. The method according to claim 1, wherein two or more enzymes are combined to form the enzyme mixture.

13. The method according to claim 1, wherein all of pepsin, trypsin, trypsin acetylated, flavourzyme, protease E and alcalase are combined to form the enzyme mixture.

14. The method according to claim 2, wherein two or more enzymes are combined to form the enzyme mixture.

15. The method according to claim 2, wherein all of pepsin, trypsin, trypsin acetylated, flavourzyme, protease E and alcalase are combined to form the enzyme mixture.

16. The method according to claim 1, wherein the substrate is selected from the group of wheat gluten and anchovy fine powder.

17. The method according to claim 16, wherein dissolving the substrate in water results in a 12% solution.

18. The method of claim 1, wherein a resulting product comprises a natural flavoring substance.

* * * * *